United States Patent
Rahdert et al.

(10) Patent No.: US 8,784,482 B2
(45) Date of Patent: *Jul. 22, 2014

(54) METHOD OF RESHAPING A HEART VALVE ANNULUS USING AN INTRAVASCULAR DEVICE

(75) Inventors: David A. Rahdert, San Francisco, CA (US); Timothy R. Machold, Moss Beach, CA (US); John A. Macoviak, La Jolla, CA (US); Robert T. Chang, Belmont, CA (US)

(73) Assignee: MVRx, Inc., Moss Beach, CA (US)

( * ) Notice: Subject to any disclaimer, the term of this patent is extended or adjusted under 35 U.S.C. 154(b) by 664 days.

This patent is subject to a terminal disclaimer.

(21) Appl. No.: 10/846,850

(22) Filed: May 14, 2004

(65) Prior Publication Data
US 2004/0260393 A1     Dec. 23, 2004

Related U.S. Application Data

(63) Continuation-in-part of application No. 10/677,104, filed on Oct. 1, 2003, now abandoned, which is a continuation-in-part of application No. 09/666,617, filed on Sep. 20, 2000, now Pat. No. 6,893,459, application No. 10/846,850, which is a continuation-in-part of application No. PCT/US02/31376, filed on Oct. 1, 2002, and a continuation-in-part of application No. 10/676,729, filed on Oct. 1, 2003, now Pat. No. 7,527,646, and a continuation-in-part of application No. 10/676,815, filed on Oct. 1, 2003, now Pat. No. 7,381,220.

(60) Provisional application No. 60/326,590, filed on Oct. 1, 2001, provisional application No. 60/429,462, filed on Nov. 26, 2002, provisional application No. 60/429,709, filed on Nov. 26, 2002, provisional application No. 60/429,444, filed on Nov. 26, 2002.

(51) Int. Cl.
*A61F 2/24* (2006.01)
*A61B 17/00* (2006.01)

(52) U.S. Cl.
CPC ..... *A61F 2/2445* (2013.01); *A61B 2017/00243* (2013.01); *Y10S 623/904* (2013.01)
USPC ........................................ 623/2.36; 623/904

(58) Field of Classification Search
CPC ................ A61F 2/2445; A61F 2/2442; A61B 17/00234; A61B 2017/00243
USPC ................ 606/151, 213; 623/2.36, 2.37, 904, 623/1.16, 1.24, 1.26; 600/37; 128/898
See application file for complete search history.

(56) References Cited

U.S. PATENT DOCUMENTS 4,056,854 A    11/1977  Boretos et al.
4,275,469 A     6/1981  Gabbay (Continued)

OTHER PUBLICATIONS

Templeton III, et al. "Experimental Reconstruction of Cardiac Valves by Venous and Pericardial Grafts." Annals of Surgery vol. 129, No. 2, Feb. 1949, 161-176.

(Continued)

*Primary Examiner* — Brian Pellegrino
(74) *Attorney, Agent, or Firm* — Ryan Kromholz & Manion, S.C.

(57) ABSTRACT

Devices, systems, and methods employ an implant that is sized and configured to attach in, on, or near the annulus of a dysfunctional heart valve. In use, the implant extends either across the minor axis of the annulus, or across the major axis of the annulus, or both. The implant restores to the heart valve annulus and leaflets a more functional anatomic shape and tension. The more functional anatomic shape and tension are conducive to coaptation of the leaflets, which, in turn, reduces retrograde flow or regurgitation.

5 Claims, 20 Drawing Sheets

(56) References Cited

U.S. PATENT DOCUMENTS

| | | | |
|---|---|---|---|
| 4,491,986 A | 1/1985 | Gabbay | |
| 4,994,069 A | 2/1991 | Ritchart et al. | |
| 5,360,444 A | 11/1994 | Kusuhara | |
| 5,370,685 A | 12/1994 | Stevens | |
| 5,716,397 A | 2/1998 | Myers | |
| 5,776,189 A | 7/1998 | Khalid | |
| 5,792,155 A | 8/1998 | Van Cleef | |
| 5,824,066 A | 10/1998 | Gross | |
| 5,830,224 A | 11/1998 | Cohn et al. | |
| 5,855,601 A | 1/1999 | Bessler et al. | |
| 5,961,440 A | 10/1999 | Schweich, Jr. et al. | |
| 6,045,497 A | 4/2000 | Schweich, Jr. et al. | |
| 6,050,936 A | 4/2000 | Schweich, Jr. et al. | |
| 6,059,715 A | 5/2000 | Schweich, Jr. et al. | |
| 6,077,214 A | 6/2000 | Mortier et al. | |
| 6,090,139 A | 7/2000 | Lemelson | |
| 6,099,542 A | 8/2000 | Cohn et al. | |
| 6,102,932 A | 8/2000 | Kurz | |
| 6,162,168 A | 12/2000 | Schweich, Jr. et al. | |
| 6,165,119 A | 12/2000 | Schweich, Jr. et al. | |
| 6,183,411 B1 | 2/2001 | Mortier et al. | |
| 6,210,432 B1 | 4/2001 | Solem et al. | |
| 6,260,552 B1 | 7/2001 | Mortier et al. | |
| 6,261,222 B1 | 7/2001 | Schweich, Jr. et al. | |
| 6,312,464 B1 | 11/2001 | Navia | |
| 6,332,864 B1 | 12/2001 | Schweich, Jr. et al. | |
| 6,332,893 B1 | 12/2001 | Mortier et al. | |
| 6,338,735 B1 | 1/2002 | Stevens | |
| 6,338,740 B1 | 1/2002 | Carpentier | |
| 6,402,781 B1 | 6/2002 | Langberg et al. | |
| 6,419,695 B1 | 7/2002 | Gabbay | |
| 6,419,696 B1 | 7/2002 | Ortiz et al. | |
| 6,440,164 B1 | 8/2002 | DiMatteo et al. | |
| 6,514,194 B2 | 2/2003 | Schweich, Jr. et al. | |
| 6,537,198 B1 | 3/2003 | Vidlund et al. | |
| 6,589,160 B2 | 7/2003 | Schweich, Jr. et al. | |
| 6,616,684 B1 | 9/2003 | Vidlund et al. | |
| 6,626,899 B2 | 9/2003 | Houser et al. | |
| 6,656,221 B2 | 12/2003 | Taylor et al. | |
| 6,669,709 B1 | 12/2003 | Cohn et al. | |
| 6,709,456 B2 | 3/2004 | Langberg et al. | |
| 6,723,038 B1 | 4/2004 | Schroeder et al. | |
| 6,764,510 B2 | 7/2004 | Vidlund et al. | |
| 6,793,618 B2 | 9/2004 | Schweich, Jr. et al. | |
| 7,291,168 B2 * | 11/2007 | Macoviak et al. | 623/2.36 |
| 2002/0032481 A1 | 3/2002 | Gabbay | |
| 2002/0065554 A1 | 5/2002 | Streeter | |
| 2002/0087169 A1 * | 7/2002 | Brock et al. | 606/139 |
| 2002/0129820 A1 | 9/2002 | Ryan et al. | |
| 2003/0040792 A1 | 2/2003 | Gabbay | |
| 2003/0078465 A1 * | 4/2003 | Pai et al. | 600/16 |
| 2003/0120340 A1 | 6/2003 | Liska et al. | |
| 2003/0233022 A1 | 12/2003 | Vidlund et al. | |
| 2004/0148019 A1 | 7/2004 | Vidlund et al. | |

OTHER PUBLICATIONS

Moore et al. "Unsuitability of Transventricular Autogenous Slings for Diminishing Valvular Insufficiency." Surgery, vol. 33, No. 2, Feb. 1953, 173-182.

Murray et al. "Reconstruction of the Valves of the Heart." The Canadian Medical Association Journal, vol. 38, No. 4, Apr. 1938, 317-319.

Bolling et al. "Early Outcome of Mitral Valve Reconstruction in Patients With End-Stage Cardiomyopathy." J Thorac Cardiovasc Surg 1995; 109:676-683.

Kameda et al. "Annuloplasty for Severe Mitral Regurgitation Due to Dilated Cardiomyopathy." Ann Thorac Surg 1996; 61:1829-1832.

Bolling et al. "Intermediate-Term Outcome of Mitral Reconstruction in Cardiomyopathy." Journal of Thoracic Cardiovascular Surgery, vol. 115, No. 2, Feb. 1998, 381-388.

Harlan et al. Manual of Cardiac Surgery, vol. 2, 1981 Figs. 16.3-16.4.

Edmunds, Jr. et al. "Septal Defect." Atlas of Cardiothoracic Surgery 1990.

Koniaris, MD et al. "Dynamic Retention: A Technique for Closure of the Complex Abdomen in Critically Ill Patients." Archives of Surgery, vol. 136, No. 12, Dec. 2001, 1359-1362.

Fucci et al. "Improved Results With Mitral Valve Repair Using New Surgical Techniques." European Journal of Cardio-Thoracic Surgery, vol. 9, 1995, 621-626.

Davila et al. "Circumferential Suture of the Mitral Ring: A Method for the Surgical Correction of Mitral Insufficiency." Journal of Thoracic Surgery Nov. 1955; 30(5): 531-60.

Harken et al. "The Surgical Correction of Mitral Insufficiency" Journal of Thoracic Surgery. Dec. 1954; 28(6):604-24.

Kuykendall et al. "Surgical Correction of Chronic Mitral Insufficiency in Dogs." Surgery. Oct. 1958; 44(4):718-25.

Harken et al. "The Surgical Correction of Mitral Insufficiency." Surgical Forum 4:4-7 1953.

Davila et al. "A Method for the Surgical Correction of Mitral Insufficiency." Surgery, Gynecology and Obstetrics Apr. 1954; 98(4):407-12.

Davila et al. "The Clinical and Physiologic Criteria for Surgical Correction of Mitral Insufficiency." Journal of Thoracic Surgery Feb. 1958; 35(2):206-31.

Glover et al. "The Treatment of Mitral Insufficiency by the Purse-String Technique." Journal of Thoracic Surgery Jan. 1957; 33(1): 75-101.

Rankin et al. "A Clinical Comparison of Mitral Valve Repair Versus Valve Replacement in Ischemic Mitral Regurgitation." J Thorac Cardiovasc Surg. Feb. 1988; 95(2):165-77.

Barnard et al. "A Surgical Approach to Mitral Insufficiency." Br J Surg. May 1961; 48:655-62.

McKenzie et al. "Current Concepts in Surgical Correction of Acquired Mitral Insufficiency." Circulation. Oct. 1963; 28:603-16.

Saab et al. "Left Ventricular Aneurysm: A New Surgical Approach." Thorac Cardiovasc Surg. Feb. 1989; 37(1):11-9.

Cicek et al. "Left Ventricular Endoaneurysmorrhaphy: Effect on Left Ventricular Size, Shape and Function." Cardiology. Jul.-Aug. 1997; 88(4):340-5.

Liedtke et al. "Functional Reductions in Left Ventricular Volume." J Thorac Cardiovasc Surg. Feb. 1976; 71(2):195-206.

Sosa et al. "Recurrent Ventricular Tachycardia Associated With Postinfarction Aneurysm. Results of Left Ventricular Reconstruction." J.Thorac Cardiovasc Surg. May 1992; 103(5); 855-60.

Cooley, "Repair of Postinfarction Ventricular Septal Defect." J Card Surg. Jul. 1994; 9(4):427-9.

Jatene, "Left Ventricular Aneurysmectomy. Resection or Reconstruction." J Thorqc Cardiovasc Surg 1985; 89:321-31.

de Silva et al. "Postinfarction Ventricular Septal Defect. An Efficacious Technique for Early Surgical Repair." J Throac Cardiovasc Surg. Jan. 1989; 97(1):86-9.

Tashiro et al. "Extended Endocardial Repair of Postinfarction Ventricular Septal Rupture: New Operative Technique-Modification of the Komeda-David Operation." J Card Surg. Mar. 1994; 9(2):97-102.

Daggett, "Surgical Technique for Early Repair of Posterior Ventricular Septal Rupture." J Thorac Cardiovasc Surg. Aug. 1982;84(2):306-12.

Daggett et al. "Surgery for Post-Myorcardial Infarct Ventricular Septal Defect." Ann Surg. Sep. 1977;186(3):260-71.

Dor, "Left Ventricular Aneurysms: the Endoventricular Circular Patch Plasty." Semin Thorac Cardiovasc Surg. Apr. 1997;9(2):123-30.

Antunes, "Submitral Left Ventricular Aneurysms. Correction by a New Transatrial Approach." J Thorac Cardiovasc Surg. Aug. 1987;94(2):241-5.

Alvarez et al. "Technical Improvements in the Repair of Acute Postinfarction Ventricular Septal Rupture." J Card Surg. Sep. 1992;7(3):198-202.

Cox, "Surgical Management of Left Ventricular Aneurysms: A Clarification of the Similarities and Differences Between the Jatene and Dor Techniques." Semin Thorqc Cardiovasc Surg. Apr. 1997;9(2):131-8.

(56) References Cited

OTHER PUBLICATIONS

Skillington et al. "Surgical Treatment for Infarct-Related Ventricular Septal Defects. Improved Early Results Combined with Analysis of Late Functional Status." J thorac Cardiovasc Surg. May 1990;99(5):798-808.

Salati et al. "Severe Diastolic Dysfunction After Endoventriculoplasty." J Thorac Cardiovasc Surg. Apr. 1995;109(4):694-701.

Yacoub et al. "Anatomic Correction of the Syndrome of Prolapsing Right Coronary Aortic Cusp, Dilatation of the Sinus of Valsalva, and Ventricular Septal Defect." J thorac Cardiovasc Surg. Feb. 1997;113(2):253-60.

Wilson, W.C., "Studies in Experimental Mitral Obstruction in Relation to the Surgical Treatment of Mitral Stenosis." The British Journal of Surgery, vol. XVIII, No. 70 ;259-74, Oct. 1930.

Bailey, et al. "Surgical Repair of Mitral Insufficiency." Diseases of the Chest, vol. XIX , No. 2, Feb. 1951, 125-137.

Henderson, et al., "The Surgical Treatment of Mitral Insufficiency." Experimental Use of Transplanted Pericardium in Dogs. Surgery 33(6):858-868; 1953.

Sakakibara, "A Surgical Approach to the Correction of Mitral Insufficiency."Annals of Surgery. vol. 142, No. 2, Aug. 1955, 196-203.

Harken et al. "The Surgical Correction of Mitral Insufficiency." The Journal of Thoracic Surgery. 28(6):604-627., 1954.

Bailey et al. "The Surgical Correction of Mitral Insufficiency by the Use of Pericardial Grafts." The Journal of Thoracic Surgery, vol. 28, No. 6, Dec. 1954, 551-603.

Kay et al. "Surgical Treatment of Mitral Insufficiency." Surgery. vol. 37, No. 5. May 1955, 697-706.

\* cited by examiner

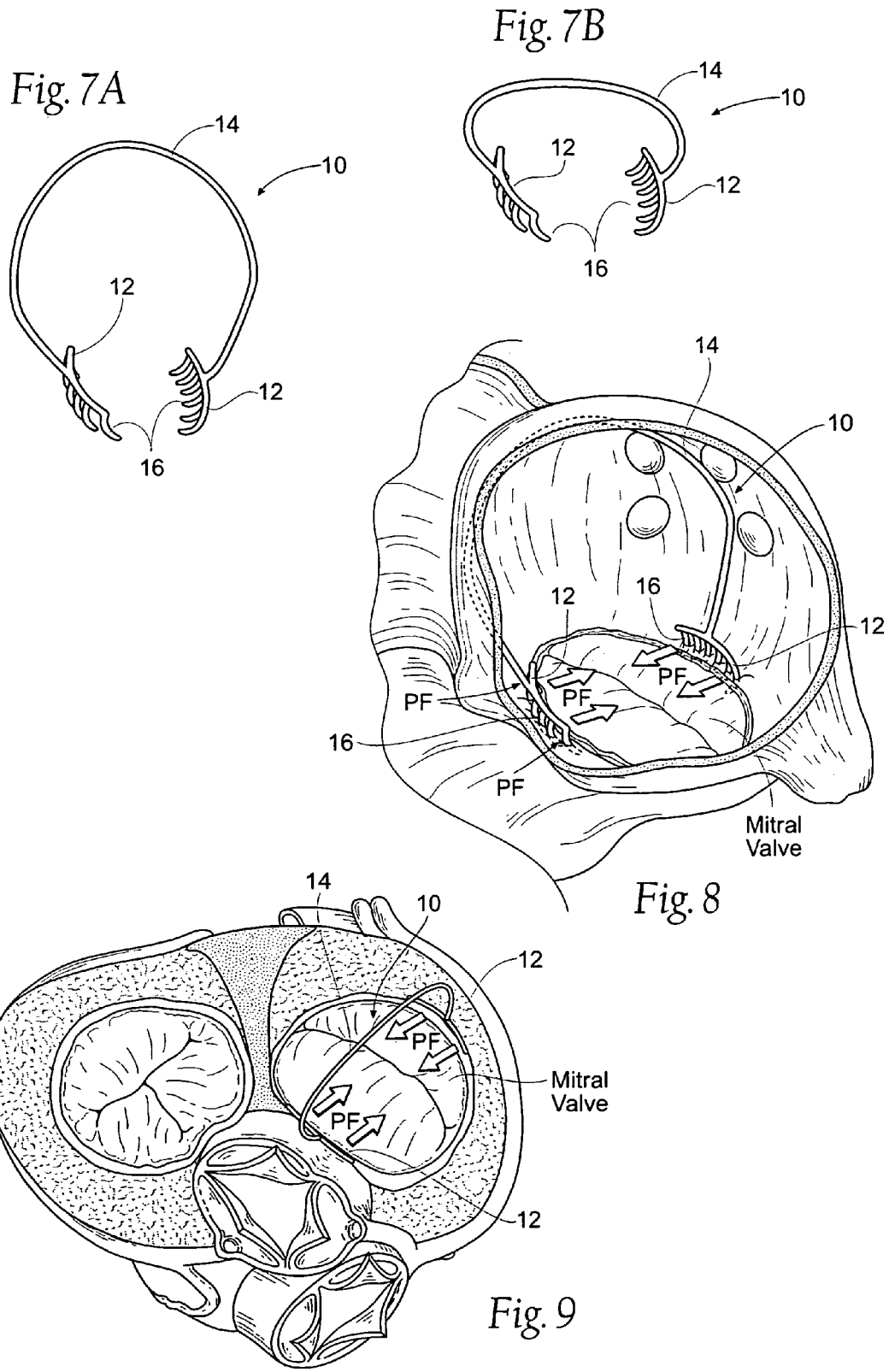

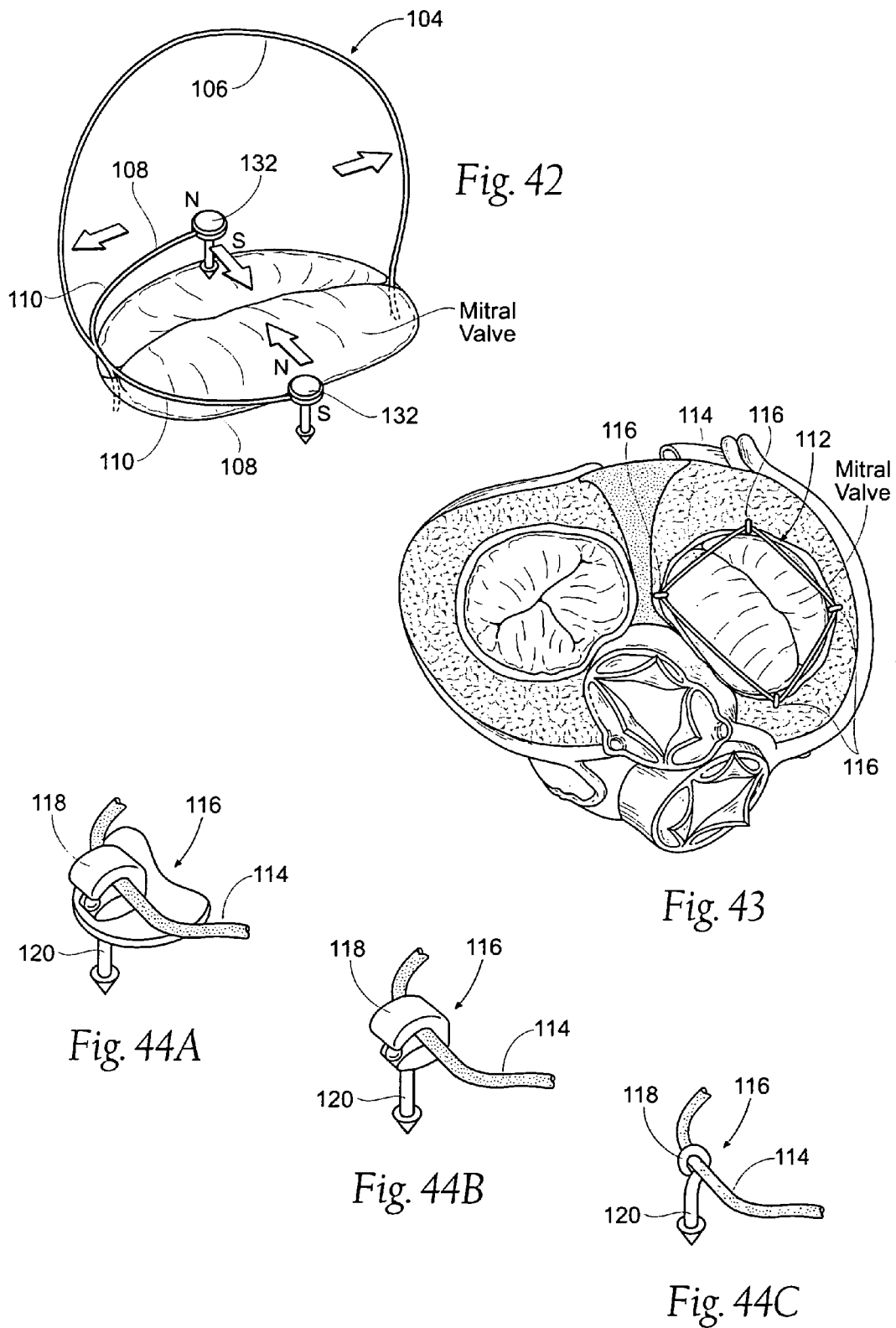

METHOD OF RESHAPING A HEART VALVE ANNULUS USING AN INTRAVASCULAR DEVICE

RELATED APPLICATIONS

This application is a continuation-in-part of U.S. patent application Ser. No. 10/677,104, filed Oct. 1, 2003 now abandoned, and entitled "Devices, Systems, and Methods for Reshaping a Heart Valve Annulus," which claims the benefit of U.S. Provisional Patent Application Ser. No. 60/429,444, filed Nov. 26, 2002, and entitled "Heart Valve Remodeling Devices," and which is a continuation-in-part of U.S. patent application Ser. No. 09/666,617, filed Sep. 20, 2000 now U.S. Pat. No. 6,893,459, and entitled "Heart Valve Annulus Device and Methods of Using Same." This application is also a continuation-in-part of Patent Cooperation Treaty Application Serial No. PCT/US 02/31376, filed Oct. 1, 2002, and entitled "Systems and Devices for Heart Valve Treatments," which claimed the benefit of U.S. Provisional Patent Application Ser. No. 60/326,590, filed Oct. 1, 2001. This application is also a continuation-in-part of U.S. patent application Ser. No. 10/676,729, filed Oct. 1, 2003 now U.S. Pat. No. 7,527,646, and entitled "Devices, Systems, and Methods for Retaining a Native heart Valve Leaflet," which claims the benefit of U.S. Provisional Patent Application Ser. No. 60/429,462, filed Nov. 26, 2002, and entitled "Heart Valve Leaflet Retaining Devices." This application is also a continuation-in-part of U.S. patent application Ser. No. 10/676,815, filed Oct. 1, 2003 now U.S. Pat. No. 7,381,220, and entitled "Devices, Systems and Methods for Supplementing, Repairing or Replacing a Native Heart Valve Leaflet," which claims the benefit of U.S. Provisional Patent Application Ser. No. 60/429,709, filed Nov. 26, 2002, and entitled "Neo-Leaflet Medical Devices."

FIELD OF THE INVENTION

The invention is directed to devices, systems, and methods for improving the function of a heart valve, e.g., in the treatment of mitral valve regurgitation.

BACKGROUND OF THE INVENTION

I. The Anatomy of a Healthy Heart

The heart (see FIG. 1) is slightly larger than a clenched fist. It is a double (left and right side), self-adjusting muscular pump, the parts of which work in unison to propel blood to all parts of the body. The right side of the heart receives poorly oxygenated ("venous") blood from the body from the superior vena cava and inferior vena cava and pumps it through the pulmonary artery to the lungs for oxygenation. The left side receives well-oxygenation ("arterial") blood from the lungs through the pulmonary veins and pumps it into the aorta for distribution to the body.

The heart has four chambers, two on each side—the right and left atria, and the right and left ventricles. The atria are the blood-receiving chambers, which pump blood into the ventricles. A wall composed of membranous and muscular parts, called the interatrial septum, separates the right and left atria. The ventricles are the blood-discharging chambers. A wall composed of membranous and muscular parts, called the interventricular septum separates the right and left ventricles.

The synchronous pumping actions of the left and right sides of the heart constitute the cardiac cycle. The cycle begins with a period of ventricular relaxation, called ventricular diastole. The cycle ends with a period of ventricular contraction, called ventricular systole.

The heart has four valves (see FIGS. 2 and 3) that ensure that blood does not flow in the wrong direction during the cardiac cycle; that is, to ensure that the blood does not back flow from the ventricles into the corresponding atria, or back flow from the arteries into the corresponding ventricles. The valve between the left atrium and the left ventricle is the mitral valve. The valve between the right atrium and the right ventricle is the tricuspid valve. The pulmonary valve is at the opening of the pulmonary artery. The aortic valve is at the opening of the aorta.

At the beginning of ventricular diastole (i.e., ventricular filling)(see FIG. 2), the aortic and pulmonary valves are closed to prevent back flow from the arteries into the ventricles. Shortly thereafter, the tricuspid and mitral valves open (as FIG. 2 shows), to allow flow from the atria into the corresponding ventricles. Shortly after ventricular systole (i.e., ventricular emptying) begins, the tricuspid and mitral valves close (see FIG. 3)—to prevent back flow from the ventricles into the corresponding atria—and the aortic and pulmonary valves open—to permit discharge of blood into the arteries from the corresponding ventricles.

The opening and closing of heart valves occur primarily as a result of pressure differences. For example, the opening and closing of the mitral valve occurs as a result of the pressure differences between the left atrium and the left ventricle. During ventricular diastole, when ventricles are relaxed, the venous return of blood from the pulmonary veins into the left atrium causes the pressure in the atrium to exceed that in the ventricle. As a result, the mitral valve opens, allowing blood to enter the ventricle. As the ventricle contracts during ventricular systole, the intraventricular pressure rises above the pressure in the atrium and pushes the mitral valve shut.

The mitral and tricuspid valves are defined by fibrous rings of collagen, each called an annulus, which forms a part of the fibrous skeleton of the heart. The annulus provides attachments for the two cusps or leaflets of the mitral valve (called the anterior and posterior cusps) and the three cusps or leaflets of the tricuspid valve. The leaflets receive chordae tendineae from more than one papillary muscle. In a healthy heart, these muscles and their tendinous cords support the mitral and tricuspid valves, allowing the leaflets to resist the high pressure developed during contractions (pumping) of the left and right ventricles.

In a healthy heart, the chordae tendineae become taut, preventing the leaflets from being forced into the left or right atria and everted. Prolapse is a term used to describe this condition. This is normally prevented by contraction of the papillary muscles within the ventricle, which are connected to the mitral valve leaflets by the chordae tendineae. Contraction of the papillary muscles is simultaneous with the contraction of the ventricle and serves to keep healthy valve leaflets tightly shut at peak contraction pressures exerted by the ventricle.

II. Characteristics and Causes of Mitral Valve Dysfunction

In a healthy heart (see FIG. 4), the dimensions of the mitral valve annulus create an anatomic shape and tension such that the leaflets coapt, forming a tight junction, at peak contraction pressures. Where the leaflets coapt at the opposing medial and lateral sides of the annulus are called the leaflet commissures, and are designated in FIG. 4 and in other Figures as CM (denoting the medial commissure) and CL (denoting the lateral commissure).

Valve malfunction can result from the chordae tendineae (the chords) becoming stretched, and in some cases tearing. When a chord tears, the result is a leaflet that flails. Also, a normally structured valve may not function properly because of an enlargement of or shape change in the valve annulus. This condition is referred to as a dilation of the annulus and generally results from heart muscle failure. In addition, the valve may be defective at birth or because of an acquired disease.

Regardless of the cause (see FIG. 5), mitral valve dysfunction can occur when the leaflets do not coapt at peak contraction pressures. As FIG. 5 shows, the coaptation line of the two leaflets is not tight at ventricular systole. As a result, an undesired back flow of blood from the left ventricle into the left atrium can occur. This condition is called regurgitation.

In some cases (see FIG. 6), the leaflets do not form a tight coaptation junction because the dimensions of the mitral valve annulus, measured along the major axis from commissure to commissure—CM to CL—and/or measured along the minor axis anterior to posterior—A to P—change. The changed dimensions no longer create the anatomic shape and tension in which the leaflets coapt at peak contraction pressures.

Comparing a healthy annulus in FIG. 4 to an unhealthy annulus in FIG. 6, the unhealthy annulus is dilated and, in particular, the anterior-to-posterior distance along the minor axis is increased. As a result, the shape and tension defined by the annulus becomes less oval (see FIG. 4) and more round (see FIG. 6). This condition is called dilation. When the annulus is dilated, the shape and tension conducive for coaptation at peak contraction pressures progressively deteriorate. Instead, at peak contraction pressures, the leaflets do not coapt completely, and a gap forms between the leaflets. During ventricular systole, regurgitation can occur through this gap. It is believed that the ratio between the commissure-to-commissure distance along the major axis and anterior-to-posterior distance along the minor axis bears a relationship to the effectiveness of leaflet coaptation. If the anterior-to-posterior distance along the minor axis increases, the ratio changes, and when the ratio reaches a certain value, regurgitation or the likelihood of regurgitation is indicated.

As a result of regurgitation, "extra" blood back flows into the left atrium. During subsequent ventricular diastole (when the heart relaxes), this "extra" blood returns to the left ventricle, creating a volume overload, i.e., too much blood in the left ventricle. During subsequent ventricular systole (when the heart contracts), there is more blood in the ventricle than expected. This means that: (1) the heart must pump harder to move the extra blood; (2) too little blood may move from the heart to the rest of the body; and (3) over time, the left ventricle may begin to stretch and enlarge to accommodate the larger volume of blood, and the left ventricle may become weaker.

Although mild cases of mitral valve regurgitation result in few problems, more severe and chronic cases eventually weaken the heart and can result in heart failure. Mitral valve regurgitation can be an acute or chronic condition. It is sometimes called mitral insufficiency.

III. Prior Treatment Modalities

In the treatment of mitral valve regurgitation, diuretics and/or vasodilators can be used to help reduce the amount of blood flowing back into the left atrium. An intra-aortic balloon counterpulsation device is used if the condition is not stabilized with medications. For chronic or acute mitral valve regurgitation, surgery to repair or replace the mitral valve is often necessary.

To date, invasive, open heart surgical approaches have been used to repair mitral valve dysfunction. During these surgical repair procedures, efforts are made to cinch or resect portions and/or fix in position large portions of the dilated annulus. During these surgical repair procedures, the annulus can be reshaped with annular or peri-annular rings or similar ring-like devices. The repair devices are typically secured to the annulus and surrounding tissue with suture-based fixation. The repair devices extend over the top and over much or all of the circumference of the annulus and leaflet surfaces.

A physician may decide to replace an unhealthy mitral valve rather than repair it. Invasive, open heart surgical approaches are used to replace the natural valve with either a mechanical valve or biological tissue (bioprosthetic) taken from pigs, cows, or horses.

The need remains for simple, cost-effective, and less invasive devices, systems, and methods for treating dysfunction of a heart valve, e.g., in the treatment of mitral valve regurgitation.

SUMMARY OF THE INVENTION

The invention provides devices, systems, and methods that employ an implant sized and configured to attach, at least in part, in, on, or near the annulus of a dysfunctional heart valve. In use, the implant extends either across the minor axis of the annulus to shorten the minor axis, or across the major axis of the annulus to lengthen the major axis, or both. The implant restores to the heart valve annulus and leaflets a more functional anatomic shape and tension. The more functional anatomic shape and tension are conducive to coaptation of the leaflets, which, in turn, reduces retrograde flow or regurgitation.

One aspect of the invention provides devices, systems, and methods that employ a multi-function implant system to affect a shape of a heart valve annulus. The system comprises a first component that is sized and configured to engage and outwardly displace tissue along a major axis of the annulus. The system also includes a second component that is sized and configured, concurrent with the first component, to engage and inwardly displace tissue along a minor axis of the annulus. The first and second components can comprise separate components or form an integrated body.

Another aspect of the invention provides devices, systems, and methods that employ an implant to affect a shape of a heart valve annulus. The implant comprises a body that includes first portion and a second portion joined to the first portion. The first portion is sized and configured to rest within a heart chamber near or within a heart valve annulus. The second portion is sized and configured to extend through a septum to rest in another heart chamber. The body can be generally aligned with a major axis of the annulus, or a minor axis of the annulus. Multiple bodies can be deployed concurrently.

Another aspect of the invention provides devices, systems, and methods that employ a magnetic force implant system to affect a shape of a heart valve annulus. The system comprises a first magnetic or ferromagnetic component sized and configured to rest in tissue at or near a heart valve annulus and a second magnetic component sized and configured to rest in tissue at or near the heart valve annulus spaced from the first magnetic component. The first and second components generate between them a magnetic field that can be either attracting or repelling. The first and second components can occupy the same heart chamber, or they can occupy different heart chambers. In one embodiment, one of the magnetic components occupies a coronary sinus.

Another aspect of the invention provides devices, systems, and methods that employ an implant that performs commissural annuloplasty. The implant comprises a body sized and configured to rest near or within an annulus of a heart valve having leaflet commissures. The body includes spaced-apart struts that are appended to the body to contact tissue at or near the leaflet commissures. The struts include elastic jaws that exert pulling forces on tissue at or near the commissures to squeeze the annulus together at the commissures to promote leaflet coaptation. The body and/or the struts and/or the jaws can comprise wire-form structures. Desirable, the body, the struts, and the jaws are collapsible for placement within a catheter.

Other features and advantages of the invention shall be apparent based upon the accompanying description, drawings, and claims.

DESCRIPTION OF THE DRAWINGS

FIGS. 7A and 7B are side perspective views of implants sized and configured to rest at or near a heart valve annulus and apply a direct mechanical force along the minor axis of the annulus to inwardly displace tissue toward the center of the annulus, the implant shown in FIG. 7A being configured to extend significantly above the plane of the valve, and the implant shown in FIG. 7B being configured to extend a short distance above the plane of the valve.

FIG. 8 is a lateral perspective view of the implant shown in FIG. 7A deployed at or near the mitral valve annulus in the left atrium.

FIG. 9 is a superior view of the implant and heart shown in FIG. 8.

FIG. 42 is a side perspective view of an alternative embodiment of a multiple function implant that is sized and configured to rest about a valve annulus to concurrently reshape the valve annulus along both major and minor axes, the implant in FIG. 42 having a major axis component that comprises an elastic member of the type shown in FIG. 28 and a minor axis component that comprises a magnetic force system of the type shown in FIG. 18A.

FIG. 43 is a superior section view of a heart showing the installation of a point loaded annuloplasty system about the mitral valve annulus.

FIGS. 44A, 44B, and 44C are perspective views of representative embodiments of clip components that accommodate passage of an elastic frame to create the point loaded annuloplasty system shown in FIG. 43.

DETAILED DESCRIPTION

Figure 1:
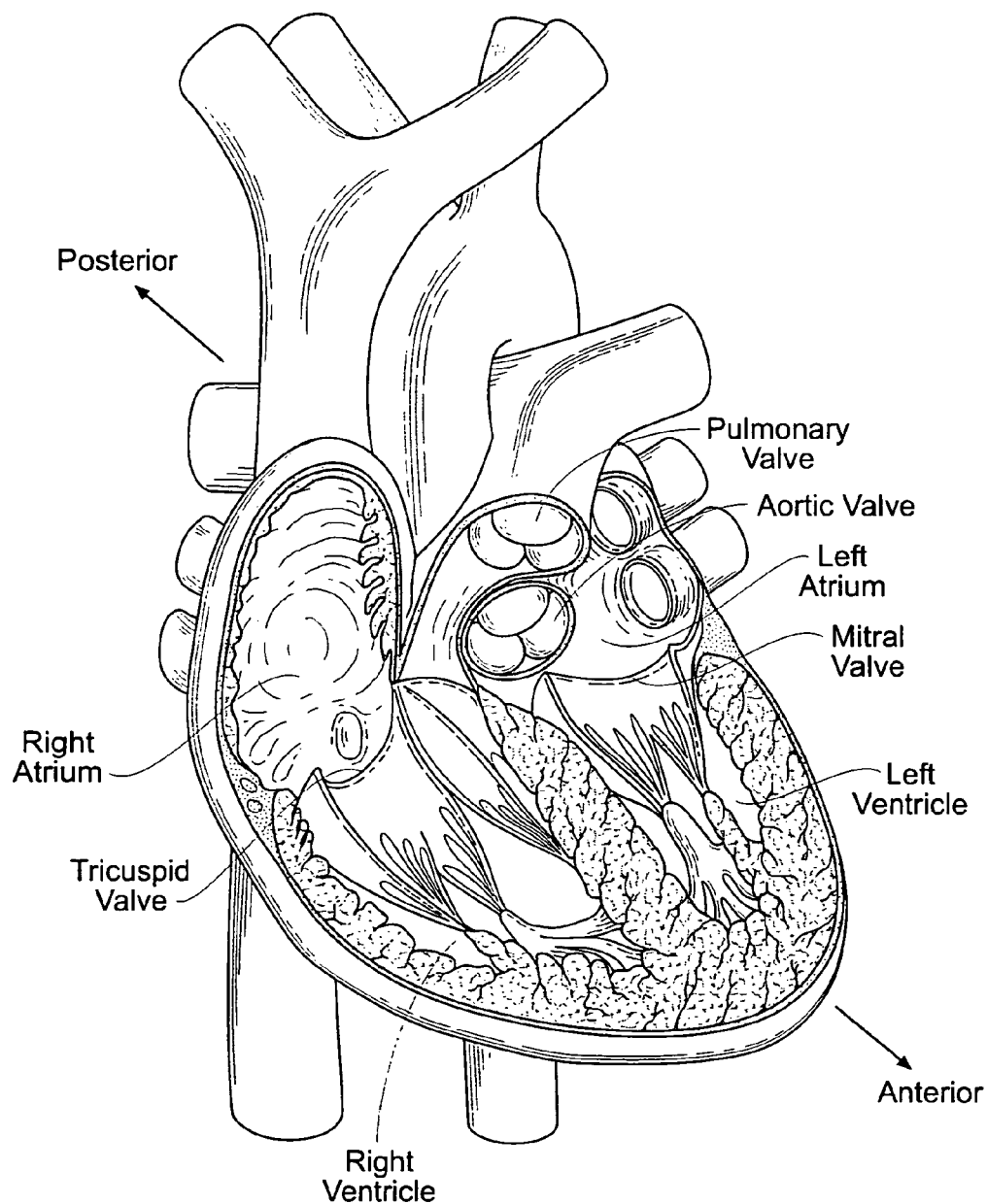
FIG. 1 is a perspective, anterior anatomic view of the interior of a healthy heart.
Figure 2:
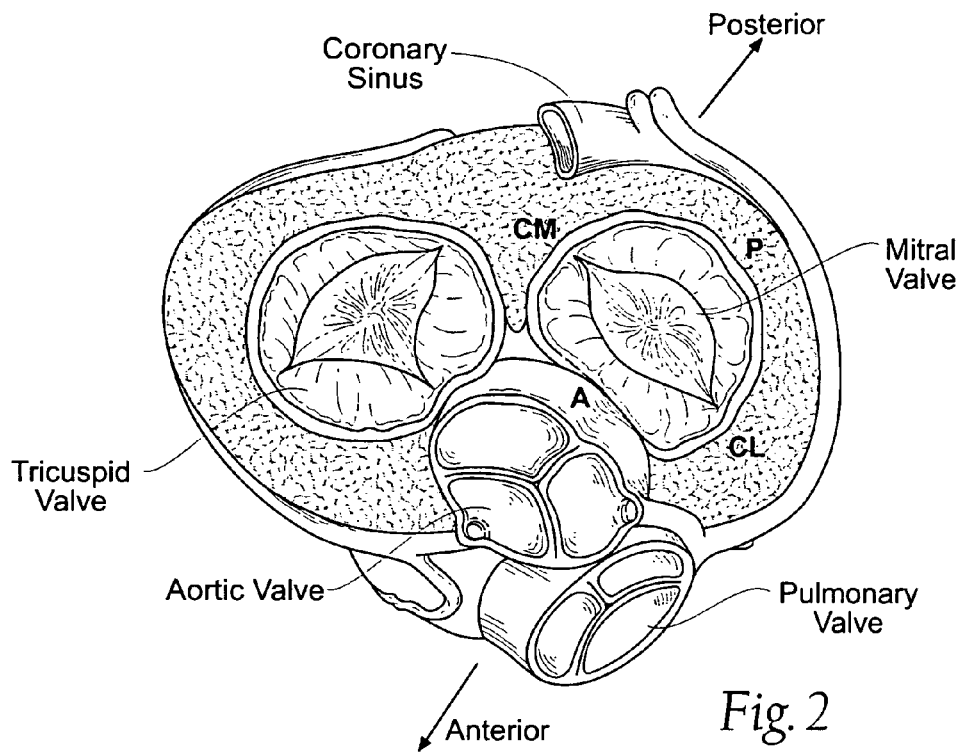
FIG. 2 is a superior anatomic view of the interior of a healthy heart, with the atria removed, showing the condition of the heart valves during ventricular diastole.
Figure 3:
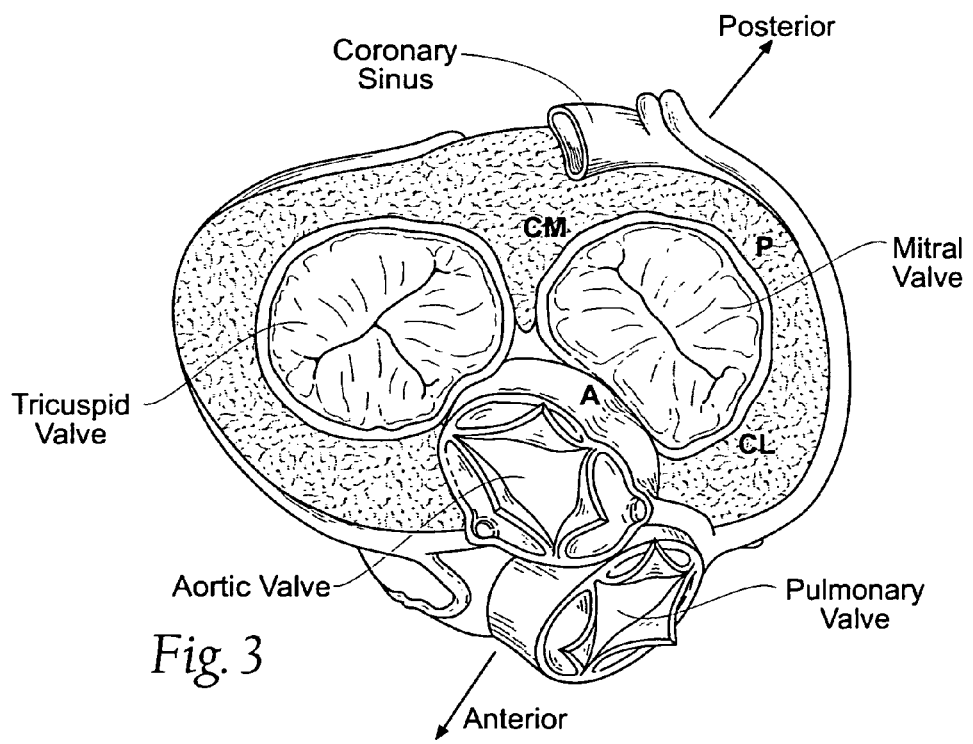
FIG. 3 is a superior anatomic view of the interior of a healthy heart, with the atria removed, showing the condition of the heart valves during ventricular systole.
Figure 4:
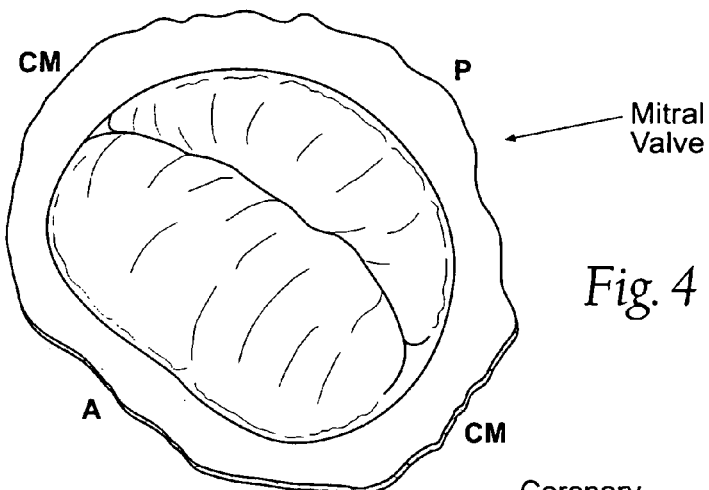
FIG. 4 is a superior anatomic view of a healthy mitral valve during ventricular systole, showing the leaflets properly coapting.
Figure 5:
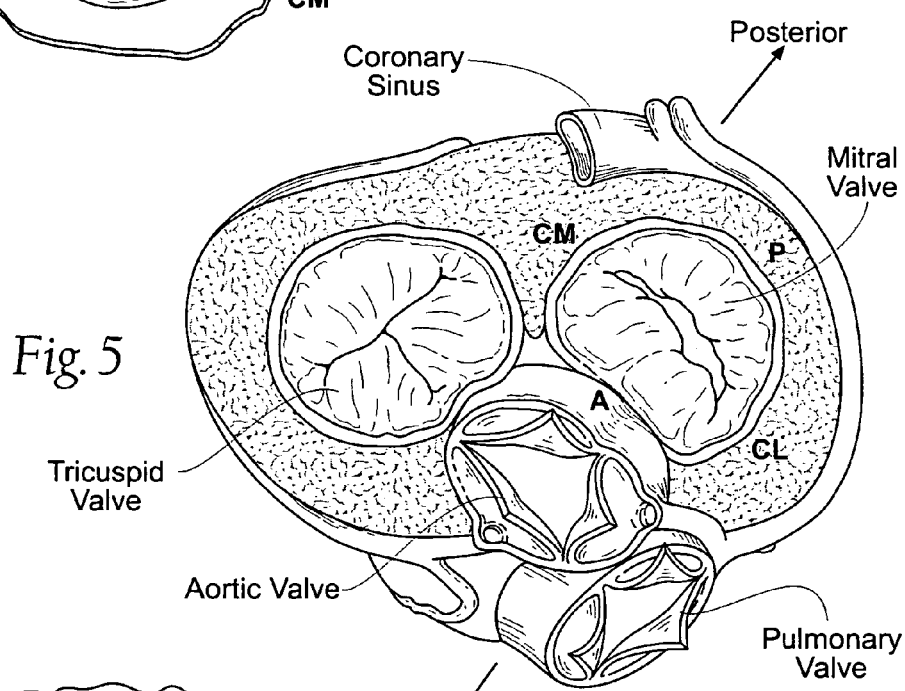
FIG. 5 is a superior anatomic view of the interior of a heart, with the atria removed, showing the condition of the heart valves during ventricular systole, and further showing a dysfunctional mitral valve in which the leaflets are not properly coapting, causing regurgitation.
Figure 6:
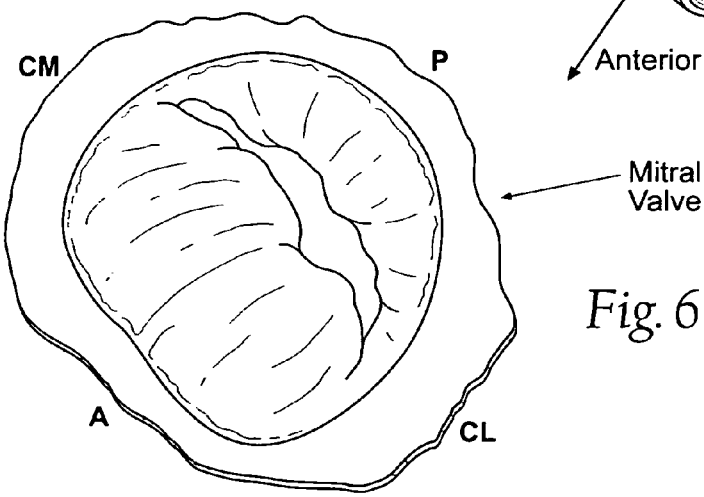
FIG. 6 is a superior anatomic view of a disfunctional mitral valve during ventricular systole, showing that the leaflets are not properly coapting, causing regurgitation.

Although the disclosure hereof is detailed and exact to enable those skilled in the art to practice the invention, the physical embodiments herein disclosed merely exemplify the invention, which may be embodied in other specific structure. While the preferred embodiment has been described, the details may be changed without departing from the invention, which is defined by the claims.

I. Implants for Direct Shortening of the Minor Axis of a Heart Valve Annulus

A. Intra-Atrial Implants

1. Structure

FIGS. 7A and 7B show embodiments of implants 10 sized and configured to rest at or near a heart valve annulus. In FIGS. 8 and 9, the embodiment of the implant 10 of FIG. 7A is shown resting in a mitral valve. In this arrangement (as FIGS. 8 and 9 show), the implant 10 extends along the minor axis (i.e., across the valve annulus in an anterior-to-posterior direction).

As FIGS. 8 and 9 show, the implant 10 is sized and shaped so that, in use, it applies a direct mechanical force along the minor axis of the annulus. The direct mechanical force serves to inwardly displace tissue (i.e., to displace tissue toward the center of the annulus) to reshape the annulus. In the illustrated embodiment (i.e., the mitral valve), the mechanical force serves to shorten the minor axis of the annulus. In doing so, the implant 10 can also reactively reshape the annulus along its major axis and/or reactively reshape other surrounding anatomic structures.

It should be appreciated that, when situated in other valve structures, the axes affected may not be the "major" and "minor" axes, due to the surrounding anatomy. It should also be appreciated that, in order to be therapeutic, the implant may only need to reshape the annulus during a portion of the heart cycle, such as during ventricular systolic contraction. For example, the implant may be sized to produce small or negligible displacement of the annulus to restore or enhance inward movement of the annulus during ventricular diastolic contraction.

The mechanical force applied by the implant 10 across the minor axis can restore to the heart valve annulus and leaflets a more normal anatomic shape and tension (see FIGS. 8 and 9). The more normal anatomic shape and tension are conducive to coaptation of the leaflets during ventricular systole, which, in turn, reduces regurgitation.

In its most basic form, the implant 10 is made—e.g., by bending, shaping, joining, machining, molding, or extrusion—from a biocompatible metallic or polymer material, or a metallic or polymer material that is suitably coated, impregnated, or otherwise treated with a material to impart biocompatibility, or a combination of such materials. The material is also desirably radio-opaque or incorporates radio-opaque features to facilitate fluoroscopic visualization.

As FIGS. 7A and 7B show, the implant 10 includes a pair of struts 12 joined by an intermediate rail 14. As FIG. 8 shows, the struts 12 are sized and configured to engage tissue at either an infra-annular position (i.e., engaging the fibrous body of the annulus) or a supra-annular position (i.e., engaging atrial tissue above or near the annulus). The rail 14 spans the struts 12. The rail 14 (like the struts 12) can take various shapes and have various cross-sectional geometries. The rail 14 (and/or the struts 12) can have, e.g., a generally curvilinear (i.e., round or oval) cross-section, or a generally rectilinear cross section (i.e., square or rectangular), or combinations thereof. In the embodiment shown in FIGS. 7A and 8, the rail 14 of the implant 10 is configured to extend significantly above the plane of the valve toward the dome of the left atrium. In the embodiment shown in FIG. 7B, the rail 14 of the implant 10 is configured to not extend significantly above the plane of the valve, but extend only enough to avoid interference with the valve leaflets.

The struts 12 each include one or more fixation elements 16. A given fixation element 16 is sized and configured to take purchase in tissue in either the infra-annular or supra-annular position. The fixation element 16 desirably relies at least partly on the valve annulus and/or neighboring anatomic structures to anchor and fix the position of the implant and resist its migration out of the annulus.

Figure 12:
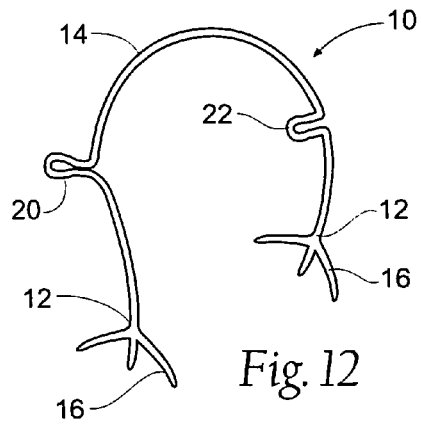
FIG. 12 is a side perspective view of an alternative embodiment of an implant sized and configured to rest at or near a heart valve annulus and apply a direct mechanical force along the minor axis of the annulus to inwardly displace tissue toward the center of the annulus, the implant shown in FIG. 12 including bell-shaped protrusions that can be grasped to aid in the positioning and/or tensioning of the implant.
Figure 13:
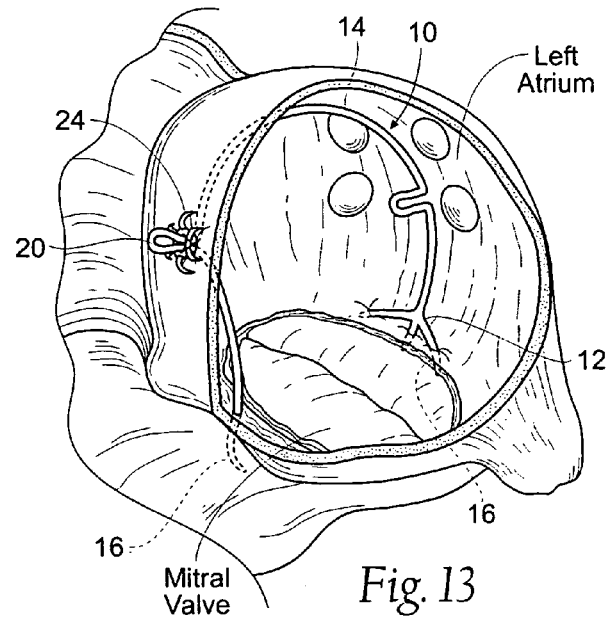
FIG. 13 is a lateral perspective view of the implant shown in FIG. 12 deployed at or near the mitral valve annulus in the left atrium, with one of the bell-shaped protrusions extending through and anchored to the septum in the right atrium.

In FIG. 7, the fixation element 16 comprises an array of barbs that penetrate tissue. FIGS. 12 and 13 (which will be described in greater detail later) show another representative embodiment for a fixation element 16, which comprises an array of tines that may contain secondary barbs in a direction that facilitates griping the tissue. Other types and forms of tissue fixation elements 16 can be used, e.g., pads with or without tissue penetrating members, and/or roughened surfaces and/or tissue in-growth promoting materials, such as polyester fabric. Any fixation element 16 may, if desired, be combined with suture, an adhesive, or like material to further secure the implant.

Being free of an appendage that extends beneath the annulus, adjustment of implant position after or during implantation is facilitated. The implant 10 also presents less chance of trauma or damage to tissue and anatomic structures beneath the annulus.

As shown in FIGS. 7 to 9, the implant 10 is desirably "elastic." The rail 14 is sized and configured to possess a normal, unloaded, shape or condition (shown in FIG. 7). In this condition, the rail 14 is not in compression or tension, and the struts 12 are spaced apart closer than the anterior-to-posterior dimension of the minor axis of the targeted heart valve annulus. The material of the implant 10 is selected to possess a desired spring constant. The spring constant imparts to the rail 14 the ability to be elastically spread apart and placed in tension out of its normal, unloaded condition, in response to external stretching forces applied at the struts.

When the struts 12 are stretched apart and anchored in tissue at or near the annulus (see FIGS. 8 and 9), the rail 14 assumes an elastically loaded, in-tension condition. When in its elastically loaded, in-tension condition, the rail 14 exerts, through the struts 12 and fixation element 16, opposing pulling forces on tissues at or near the annulus. These forces are shown by arrows marked PF in FIGS. 8 and 9. The pulling forces inwardly displace tissue and shorten the annulus along its minor axis. The pulling forces can also reshape the major axis and/or surrounding anatomic structures. In this way, the implant 10 can reshape the valve annulus toward a shape more conducive to leaflet coaptation.

An elastic implant as described can be made, e.g., from superelastic alloy, like Nitinol material. In this arrangement, the implant can also be elastically straightened and/or folded to fit within a catheter or sheath during deployment, and will regain a preferred shape upon deployment.

The spring constant of the implant 10 may be selected to be greater than the spring constant of adjoining tissue. Alternatively, the spring constant of the implant 10 may be selected to approximate the spring constant of adjoining tissue, thereby providing compliance to allow the implant 10 to adapt to tissue morphology during use. The spring constant of the implant 10 may vary along the length of the rail 14, so that some portions of the rail 14 are stiffer or more compliant than other portions of the rail 14.

2. Implantation

The implant 10 as just described and shown in either FIG. 7A or 7B lends itself to implantation in a heart valve annulus in various ways. The implant 10 can be implanted, e.g., in an open heart surgical procedure. Alternatively, the implant 10 can be implanted using catheter-based technology via a peripheral venous access site, such as in the femoral or jugular vein or femoral artery, under image guidance. Alternatively, the implant 10 can be implanted using thoracoscopic means through the chest, or by means of other surgical access through the right atrium, also under image guidance. Image guidance includes but is not limited to fluoroscopy, ultrasound, magnetic resonance, computed tomography, or combinations thereof.

FIGS. 10 and 11 show a representative embodiment of the deployment of an elastic implant 10 of the type shown in FIGS. 7A, 8, and 9 by a percutaneous, catheter-based procedure, under image guidance.

Figure 10A:
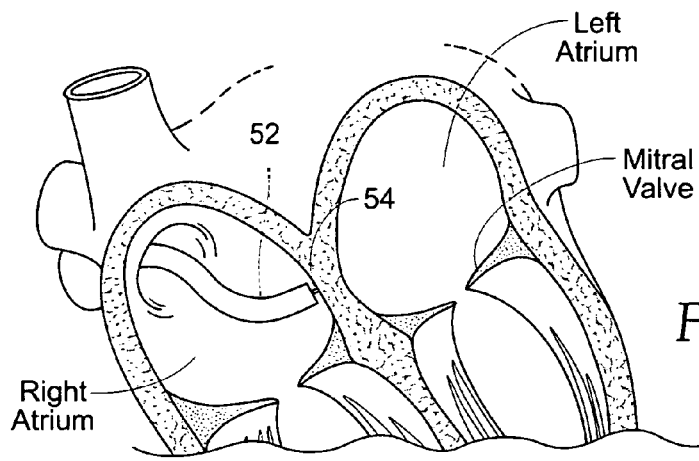
FIGS. 10A, 10B, and 10C are perspective anterior views of the intravascular deployment of a catheter from the right atrium across the septum into the left atrium for the purpose of implanting an implant of the type shown in FIG. 7A.
Figure 10B:
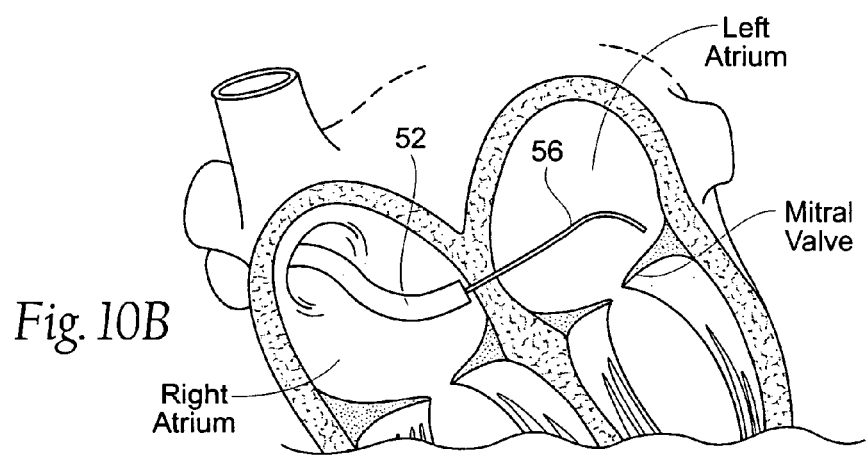
Figure 10C:
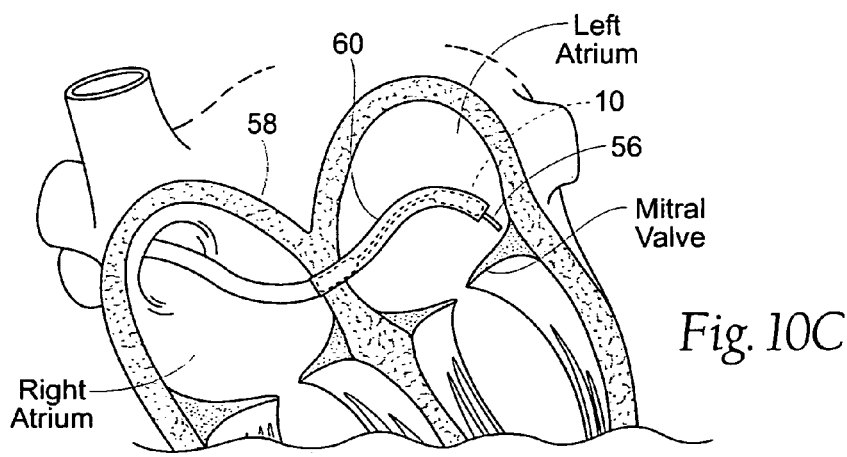

Percutaneous vascular access is achieved by conventional methods into the femoral or jugular vein. As FIG. 10A shows, under image guidance, a catheter 52 is steered through the vasculature into the right atrium. A needle cannula 54 carried on the distal end of the catheter is deployed to pierce the septum between the right and left atrium. As FIG. 10B shows, a guide wire 56 is advanced trans-septally through the needle catheter 52 into the left atrium. The first catheter 52 is withdrawn (as FIG. 10C shows), and under image guidance, an implant delivery catheter 58 is advanced over the guide wire 56 into the left atrium into proximity with the mitral valve. Alternatively, the implant delivery catheter 58 can be deployed trans-septally by means of surgical access through the right atrium.

The implant delivery catheter 58 carries a sheath 60 at its distal end (see FIG. 10C). The implant 10 is constrained in a collapsed, straightened condition within the sheath. The sheath 60 is sized and configured to be withdrawn (e.g., by sliding it proximally), to progressively free the implant 10. Progressively freed from the sheath 60, the elastic implant 10 will expand and take shape. Alternatively, a flexible push rod in the catheter 58 can be used to expel the implant 10 from the sheath 60, with the same result.

Figure 11A:
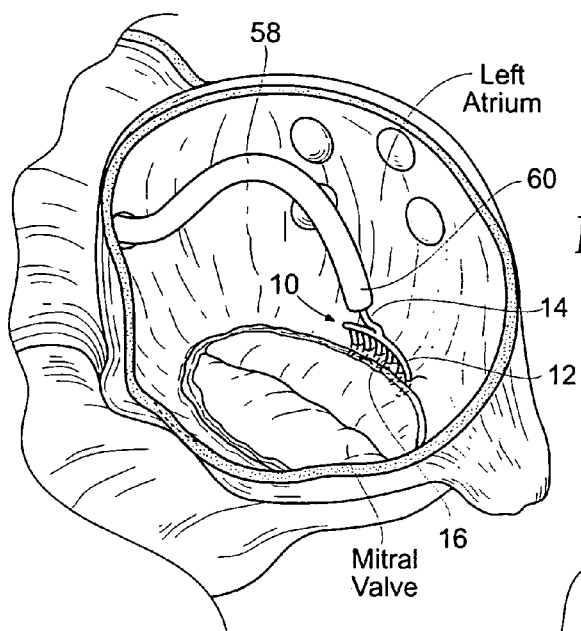
FIGS. 11A, 11B, and 11C are lateral perspective views of the sequential deployment of the implant shown in FIG. 7A from the catheter shown in FIGS. 10A, 10B, and 10C in the left atrium, with a balloon being shown in FIG. 11C inflated to place the implant into tension across the minor axis of the mitral valve.
Figure 11B:
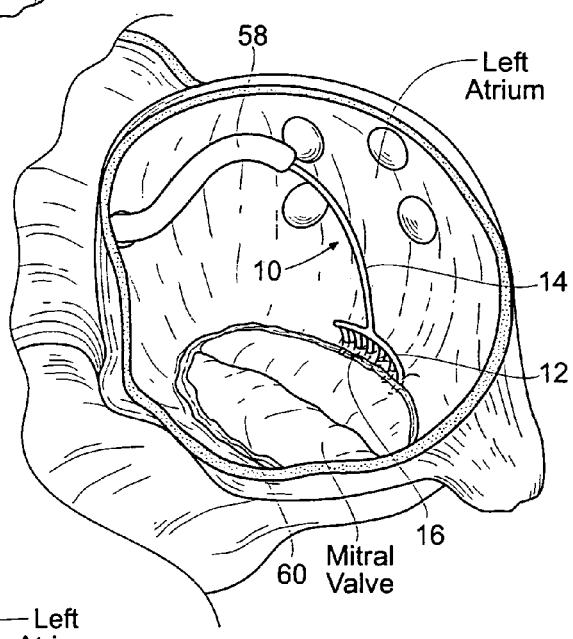
Figure 11C:
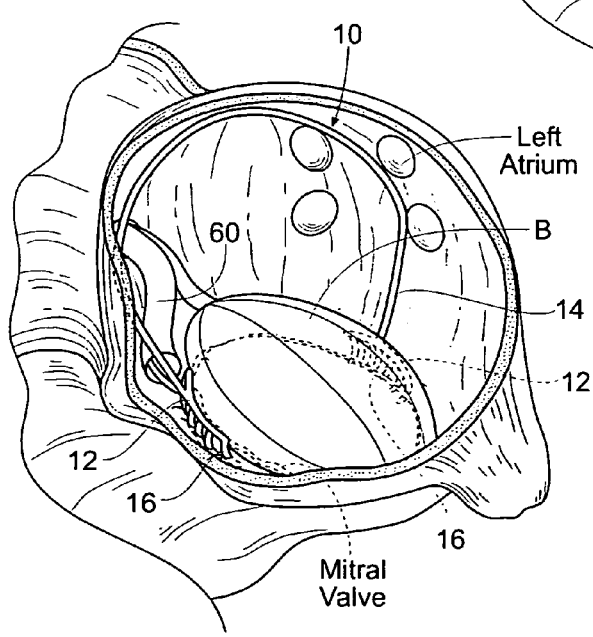

Desirably, the struts 12 are folded within the sheath 60 to reduce the collapsed profile and facilitate the expansion of the implant 10 once free of the sheath 60. As FIG. 11A shows, under image guidance, the strut 12 on the posterior end of the implant 10 is first freed from the sheath 60. The posterior strut 12 is manipulated to place the fixation element 16 into tissue in or near the posterior annulus. As FIG. 11B shows, the delivery catheter 58 maintains force on the posterior strut 12, as the sheath 60 is further withdrawn, as the catheter tracks across the minor axis of the annulus in a posterior-to-anterior direction. The delivery catheter 58 may be sized and configured to have the column strength sufficient to maintain force on the posterior strut. Progressively freed from the sheath 60, the elastic implant 10 takes shape (see FIG. 11C), until the anterior strut 12 unfolds. The rail 14 can be placed into tension, e.g., using a balloon B and/or catheter-deployed grasping instruments, to seat the fixation element 16 of the anterior strut 12 in tissue at or near the anterior annulus. Once seated, the strut 12 is released by the catheter 58.

In an alternative embodiment (see FIG. 12), the implant 10 includes bell-shaped protrusions 20 and 22 formed, respectively, along anterior and posterior portions of the rail 14. As FIG. 13 shows, the anterior protrusion 20 is sized and configured to, when implanted, extend through the septum and project into the right atrium. There, the anterior protrusion 20 is exposed for manipulation by a suitable grasping instrument deployed in the right atrium. For example, the grasping instrument can take hold of the protrusion 20 in the right atrium to facilitate placement of the rail 14 in tension within the left atrium. The posterior protrusion 22 within the left atrium can also be grasped by an instrument in the left atrium, to aid in positioning and/or for tensioning the rail.

As FIG. 13 shows, barbed stays 24 braced against the septum can be crimped to the anterior protrusion 20, to help maintain a desired degree of tension on the rail 14 in the left atrium.

Furthermore, the projection of the anterior protrusion 20 into the right atrium facilitates repositioning and/or retrieval of the implant 10 from the right atrium, when desired.

B. Trans-Septal Implants

1. Structure

Figure 14:
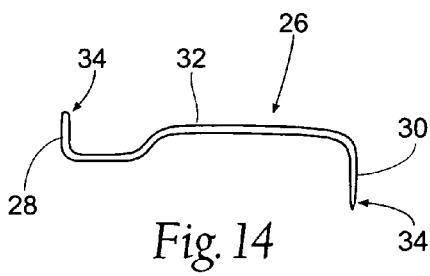
FIG. 14 is a side view of an alternative embodiment of an implant sized and configured to rest at or near a heart valve annulus and apply a direct mechanical force along the minor axis of the annulus to inwardly displace tissue toward the center of the annulus, the implant shown in FIG. 14 having an anterior component that is sized and configured to pass through the septum and project into the right atrium.
Figure 15:
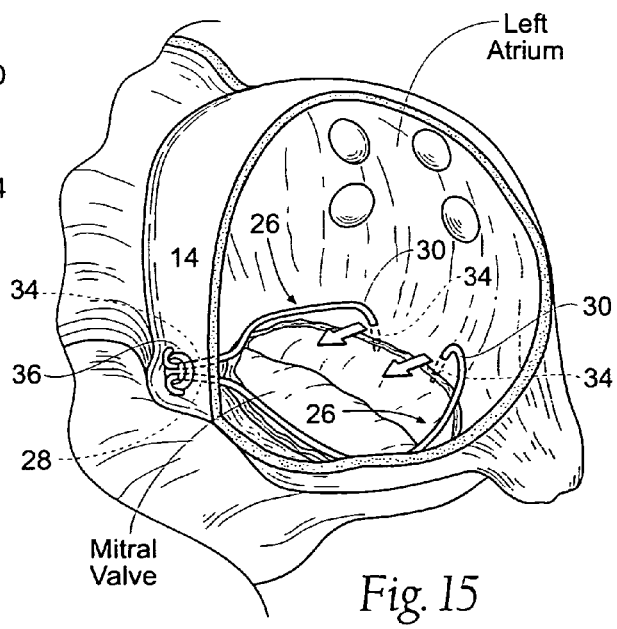
FIG. 15 is a lateral perspective view of a pair of the implants shown in FIG. 14 deployed at or near the mitral valve annulus in the left atrium, with the anterior component extending through and anchored to the septum in the right atrium.
Figure 16:
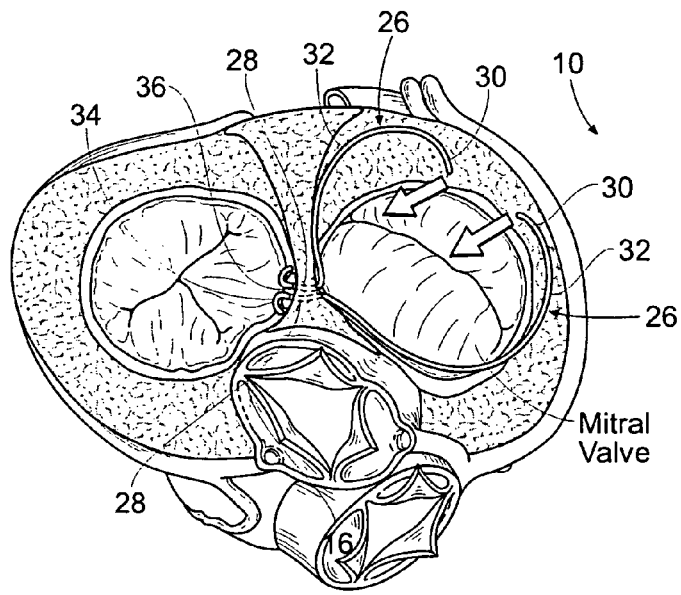
FIG. 16 is a superior view of the implants and the heart shown in FIG. 15.

FIG. 14 shows another embodiment of an implant 26, which is sized and configured to apply a mechanical force along the minor axis of a heart valve, or to otherwise stabilize tissue adjacent a heart valve annulus, and, in particular, a mitral heart valve annulus, as FIGS. 15 and 16 show. In the illustrated embodiment, and as described in connection with the implant 10 shown in FIG. 7, the mechanical force that is applied by the implant 26 in FIGS. 15 and 16 (shown by arrows) serves to inwardly displace tissue (i.e., to displace tissue toward the center of the annulus) (see FIGS. 15 and 16), to shorten the minor axis and reshape the valve. As previously described, the mechanical force directly applied by the implant 26 across the minor axis can also reactively reshape the major axis of the annulus as well as reshape other surrounding anatomic structures. The implant 26 can restore the heart valve annulus and leaflets to a more normal anatomic shape and tension conducive to coaptation of the leaflets during ventricular systole, which, in turn, reduces regurgitation. It should be appreciated, however, the presence of the implant 26 may serve to stabilize tissue adjacent the heart valve annulus, without affecting the length of the minor axis.

As shown in FIG. 14, the implant 26 is made—e.g., by bending, shaping, joining, machining, molding, or extrusion—from a biocompatible metallic or polymer material, or a metallic or polymer material that is suitably coated, impregnated, or otherwise treated with a material to impart biocompatibility, or a combination of such materials. The material is also desirably radio-opaque to facilitate fluoroscopic visualization.

As shown in FIG. 14, the implant 26 includes a pair of struts 28 and 30 joined by an intermediate rail 32. The rail 32 (like the struts 28 and 30) can take various shapes and have various cross-sectional geometries. The rail 32 (and/or the struts 28 and 30) can have, e.g., a generally curvilinear (i.e., round or oval) cross-section, or a generally rectilinear cross section (i.e., square or rectangular), or combinations thereof.

The struts 28 and 30 at one or both ends of the rail 32 may include a fixation element 34 to enhance fixation in tissue. Various tissue fixation elements 34 can be used, e.g., tissue penetrating barbs (as shown), pads with roughened surfaces or tissue in-growth promoting materials, such as polyester fabric. Any fixation element 34 may, if desired, be combined with suture, an adhesive, or like material to further secure the implant.

As shown in FIGS. 15 and 16 show, the fixation element 34 on the posterior strut 30 is sized and configured to engage tissue at either an infra-annular position (i.e., engaging the fibrous body of the annulus) or a supra-annular position (i.e., engaging atrial tissue) above or near the posterior annulus within the left atrium.

The fixation element 34 on anterior strut 28 is sized and configured to pass through the septum and project into the right atrium. There, the fixation element 34 itself can engage tissue in the septum. Alternatively, as FIGS. 15 and 16 show, the fixation element 34 can include an anchor button 36. The anchor button 36 captures the anterior strut 28 and holds the anterior strut 28 against the septum in the right atrium.

2. Implantation

Figure 17A:
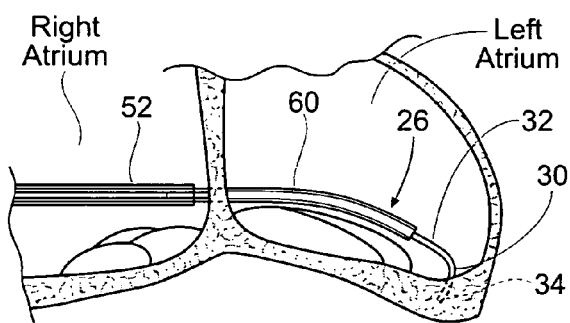
FIGS. 17A and 17B are lateral side views of the deployment of one of the implants shown in FIGS. 15 and 16 from the right atrium and through the septum into the left atrium.

The implant 26 can be deployed within a catheter 52 from the right atrium into the left atrium, in the same manner shown in FIGS. 10A, 10B, and 10C. The fixation element 34 on the posterior strut 30 is positioned in engagement with tissue in either an infra-annular or supra-annular location the posterior annulus (as FIG. 17A shows), and the anterior strut 28 is lead through the septum (as FIG. 17B shows).

Figure 17B:
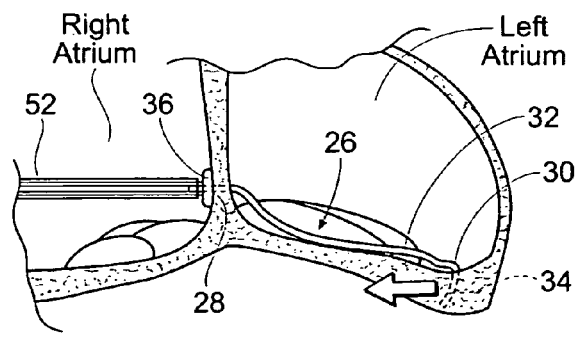

As FIG. 17B shows, pulling on the anterior strut 28 within the right atrium (i.e., through the septum) exerts a pulling force on tissue at or near the posterior annulus (shown by an arrow in FIG. 17B). The pulling force draws the posterior annulus inwardly toward the anterior annulus, thereby shortening the annulus along its minor axis. As previously described, the pulling forces can also reactively reshape the annulus along its major axis, as well as reshape surrounding anatomic structures. In this way, the implant reshapes the valve annulus toward a shape more conducive to leaflet coaptation, just as the implant 10 previously described.

As shown in the embodiment illustrated in FIGS. 15 and 16, at least two of the implants 26 are desirably used concurrently, to distribute pulling forces along medial and lateral sides of the minor axis. In this arrangement, the fixation elements 34 on the posterior struts 30 take purchase in tissue within the left atrium in spaced-apart locations above or near or in the posterior annulus. The fixation elements 34 on the anterior struts 28 jointly pass through the septum. Pulling on the anterior struts 28 from within the right atrium draws the posterior annulus toward the anterior annulus, thereby shortening the annulus across its minor axis. The anterior struts 28 can be pulled individually or concurrently to achieve the reshaping desired.

In this arrangement, as FIG. 16 best shows, one implant 26 is shaped to direct force outward toward the septum wall of the left atrium, while the other implant 26 is shaped to direct force outward toward the lateral wall of the left atrium. The resulting forces are uniformly distributed along the posterior annulus.

Once the desired degree of pulling force is established, the anterior struts 28 can be jointly fixed against the septum by the anchor button 36. As before described, the fixation elements 34 themselves can apply the holding force, without use of the anchor button 36.

C. Magnetic Force Systems

1. Structure

Figure 18A:
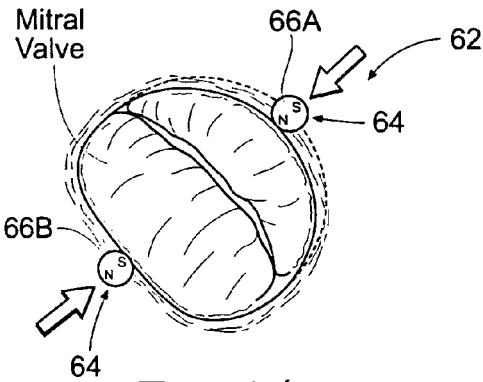
FIGS. 18A and 18B are superior views of a mitral valve annulus having different embodiments of magnetic force systems implanted at or near the annulus, to generate a magnetic field that attract tissue regions of the annulus toward one another, the magnetic force systems being arranged to shorten the minor axis of the annulus.

FIGS. 18A/B/C and 19A/B show various embodiments of a magnetic force system 62 that, in use, shortens an axis of a heart valve using one or more implanted magnetic elements 64. The implanted magnetic elements 64 generate magnetic field forces that attract tissue regions of the annulus toward one another.

As shown in FIGS. 18A/B/C to 19A/B, the tissue regions comprise the posterior and anterior edges of a mitral valve annulus. The magnetic field forces draw the tissue regions closer together across the minor axis of the annulus. The minor axis of the annulus is thereby shortened. As already described, shortening of the minor axis can reshape the valve, as well as reshape other surrounding anatomic structures, to restore the heart valve annulus and leaflets to a more normal anatomic shape and tension conducive to coaptation of the leaflets during ventricular systole, which, in turn, reduces regurgitation.

Figure 18B:
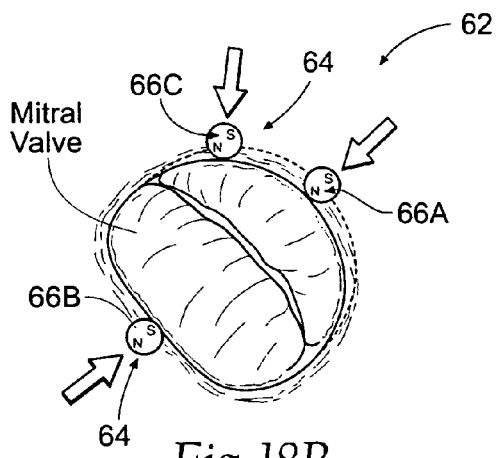

In FIGS. 18A and 18B, the magnetic elements 64 comprise two or more permanent magnets 66. Permanent magnets 66 can comprise, e.g., alloys of Neodymium-Iron-Boron (NdFeB), alloys of Aluminum-Nickel-Cobalt (AlNiCo), and Samarium Cobalt (SmCo). A permanent magnet 66 generates an external magnetic field. As FIGS. 18A and 18B shows, two permanent magnets 66A and 66B are affixed on or above the annulus in the left atrium, with opposite magnetic poles facing each other (North-South or South-North). Poles of opposite polarity attract each other with a magnetic force. The force of magnetic attraction depends on the strength of the magnets and the distance between them.

Figure 18C:
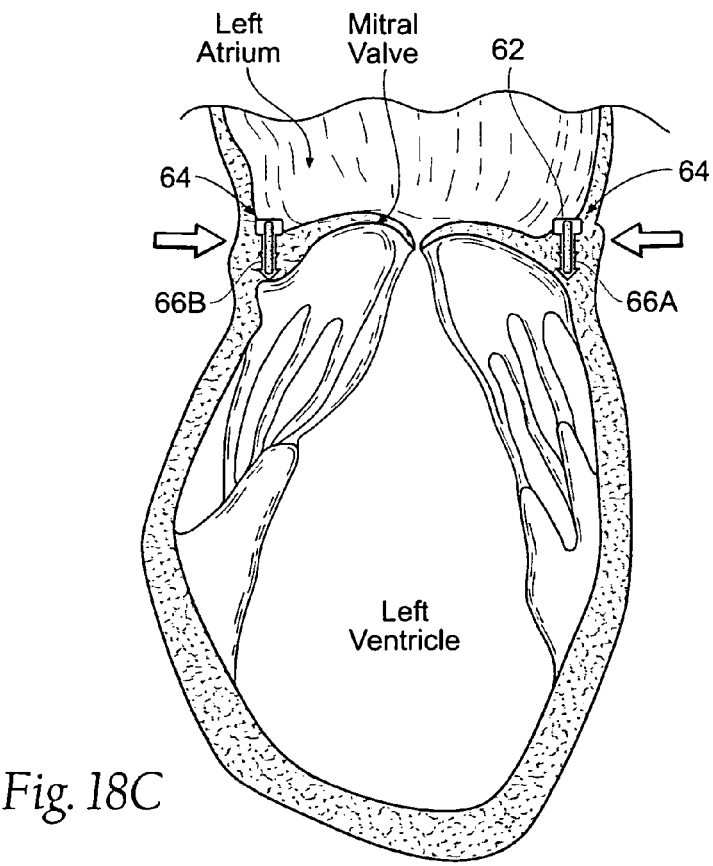
FIG. 18C is an anterior side view of the magnetic force systems shown in FIGS. 18A and 18B.

In FIGS. 18A and 18B, two permanent magnets 66A and 66B of opposite polarity are affixed, respectively, on or above the anterior and posterior regions of the annulus, aligned generally across the minor axis of the annulus. The force of magnetic attraction (shown by arrows) draws the posterior annulus and the anterior annulus toward one another, shortening the minor axis (see FIG. 18C also).

In FIG. 18B, at least one additional permanent magnet 66C is provided on or above the posterior annulus on one or both sides of the magnet aligned on the minor axis. The additional permanent magnet 66C has a pole facing the adjacent minor axis magnet 66A that is like the pole of the adjacent minor axis magnet. Poles of like polarity repel each other with a magnetic force. The force of magnetic repulsion pushes the additional permanent magnet 66C and the adjacent minor axis magnet 66A apart, keeping the two magnets 66A and 66C on the posterior annulus apart and stretching tissue between the magnets 66A and 66C. At the same time, due to the presence of an additional permanent magnet, the force of magnetic attraction between the permanent magnets 66A and 66C on the posterior annulus and the anterior annulus 66B is amplified, further enhancing the force that draws the posterior annulus and the anterior annulus toward one another, shortening the minor axis.

Figure 19A:
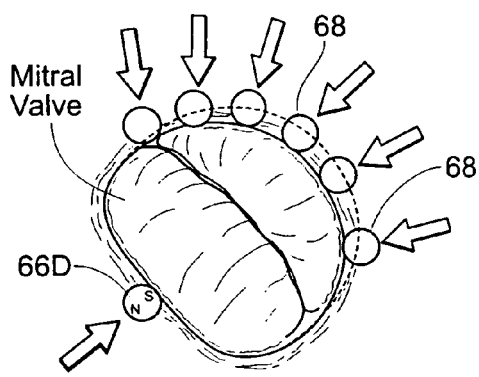
FIGS. 19A and 19B are superior views of a mitral valve annulus with other alternative embodiments of implanted magnetic force systems of the types shown in FIGS. 18A, 18B, and 18C implanted at or near the annulus, to generate a magnetic field that attract tissue regions of the annulus toward one another to shorten the minor axis of the annulus.
Figure 19B:
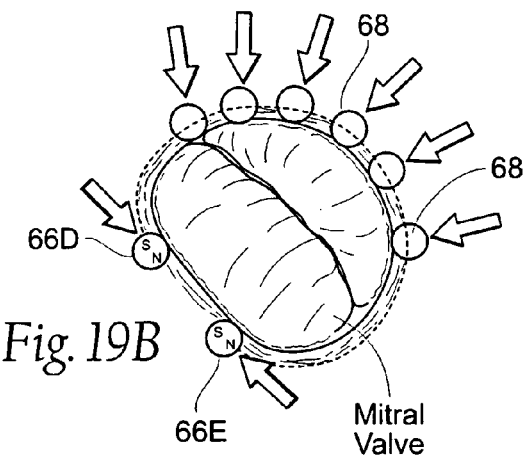

In FIGS. 19A and 19B, a permanent magnet 66D is affixed on or above either the anterior annulus or the posterior annulus generally aligned with the minor axis. In FIGS. 19A and 19B, the permanent magnet 66D is shown affixed on or above the anterior annulus. On the opposite annulus (which, in FIGS. 19A and 19B, comprises the posterior annulus), an array of soft ferromagnetic materials 68, e.g. Iron (Fe), is affixed.

Soft magnetic materials 68 are attracted by a permanent magnet 66D. The force of magnetic attraction draws the posterior annulus and the anterior annulus toward one another, shortening the minor axis. The force of attraction can be strengthened (see FIG. 19B) by affixing an additional permanent magnet 66E on or above the anterior annulus adjacent the minor axis permanent magnet 66D. As described with respect to the embodiment shown in FIG. 18B, the additional permanent magnet 66E has a pole facing the adjacent minor axis magnet that is like the pole of the adjacent minor axis magnet 66D. The force of magnetic repulsion pushes the additional permanent magnet and minor axis magnet apart, keeping the two magnets on the anterior annulus spaced apart and stretching tissue between the two magnets 66D and 66E.

Figure 20:
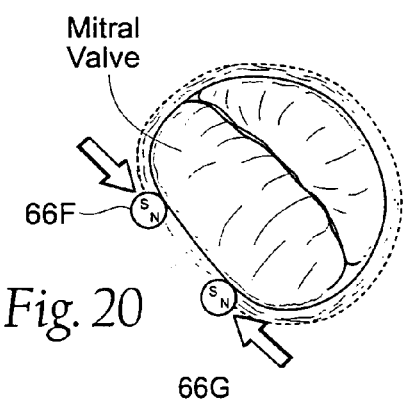
FIG. 20 is a superior view of a mitral valve annulus with an alternative embodiment of an implanted magnetic force system implanted at or near the annulus along one side of the annulus, to generate a magnetic field that attract tissue regions along that side of the annulus toward one another.

As shown in FIG. 20, two or more permanent magnets 66F and 66G having opposite magnetic poles can be affixed on or above given regions of the annulus (here, the anterior annulus), without companion, oppositely spaced magnets. The force of magnetic attraction draws the permanent magnets together, stretching the tissue along the circumference of the posterior annulus. The magnetic force field reshaping occasioned in this arrangement shortens the minor axis, reshaping the annulus.

Figure 21:
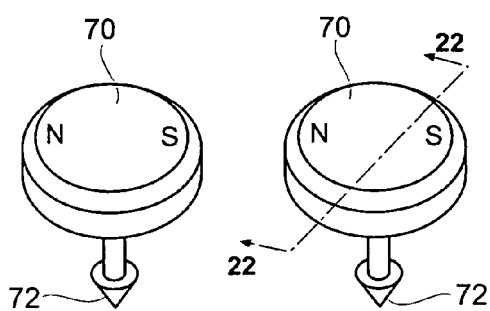
FIG. 21 is a representative embodiment of button-shaped magnetic elements that can be used to create the magnetic force systems shown in FIGS. 18A, 18B, 18C, 19A, 19B, and 20.
Figure 22:
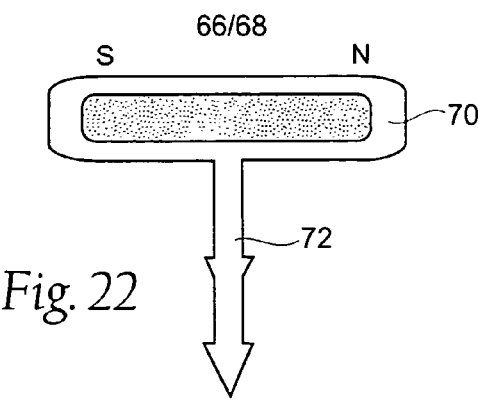
FIG. 22 is a side section view of a button-shaped magnetic element taken generally along line 22-22 is FIG. 21.

As FIGS. 21 and 22 show, the permanent magnets 66 and/or soft ferromagnetic materials 68 can be machined, laser cut, chemically etched, or EDM manufactured into packets 70 of various shapes. The packets 70 are desirably encased or packaged in an inert, insulation material, such as gold. The packets include one or more fixation elements 72, which anchor the packets 70 in tissue on or above the targeted valve annulus.

In FIGS. 21 and 22, the packets 70 are button-shaped, and the fixation elements 72 comprise barbs that penetrate tissue. Other shapes and configuration can, of course, be used.

Figure 23A:
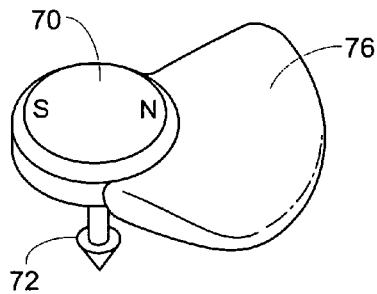
FIGS. 23A and 23B are a representative embodiment of a button-shaped magnetic element that can be used to create the magnetic force systems shown in FIGS. 18A, 18B, 18C, 19A, 19B, and 20, the magnetic element including a leaflet retaining appendage that overlays a native valve leaflet, FIG. 23A being a side perspective view and FIG. 23B being a side section view of the magnetic element and appendage.
Figure 23B:
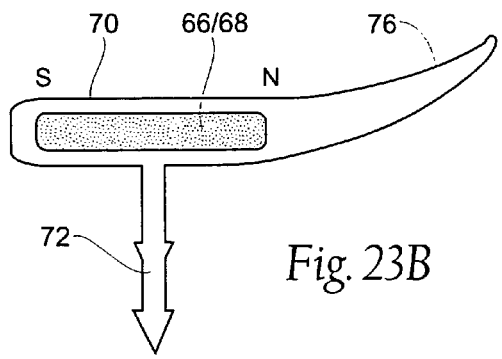
Figure 24:
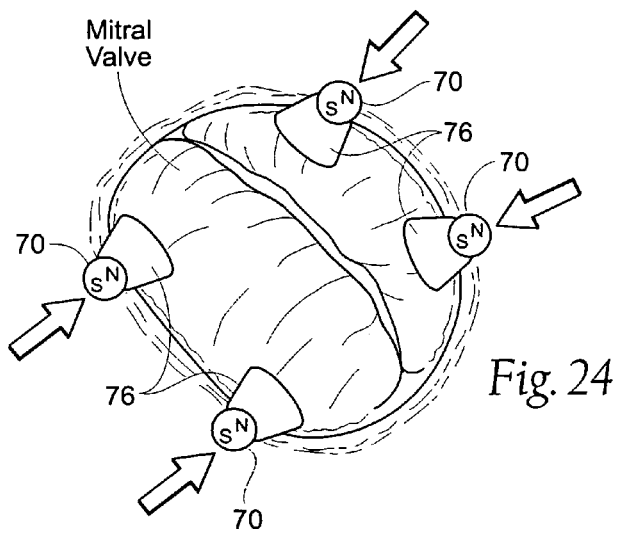
FIG. 24 is a superior view of a mitral valve with the magnetic elements shown in FIGS. 23A and 23B implanted along opposite anterior and posterior sides of the annulus.

In FIG. 23A/B, the packet 70 is button-shaped and further includes a leaflet retaining appendage 76. When anchored into tissue on or above an annulus (see FIG. 24), the leaflet retaining appendage 76 overlays at least a portion of one or more native valve leaflets. The leaflet retaining appendage 76 resists leaflet eversion and/or prolapse. In this way, a system of magnetic implants not only reshapes the valve annulus along the minor axis, but also prevents or reduces retrograde flow and regurgitation. The leaflet retaining appendage 76 does not interfere with the opening of and blood flow through the leaflets during antegrade flow.

Figure 25:
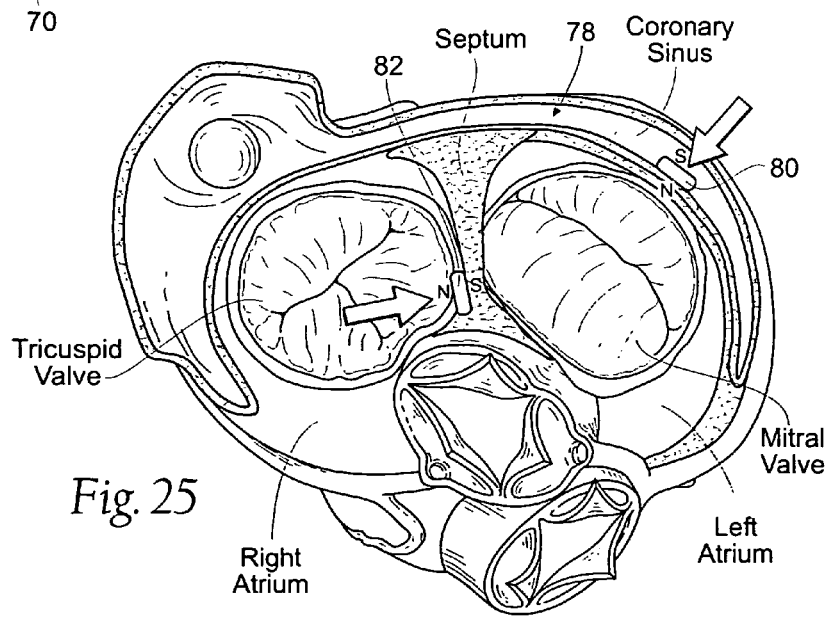
FIG. 25 is a superior view of a heart showing the presence of a magnetic force system having one magnetic element implanted within the coronary sinus above the posterior annulus of the mitral valve and a second magnetic element implanted on the septum in the right atrium close to the anterior annulus of the mitral valve, to create between them a force of magnetic attraction that shortens the minor axis of the mitral valve.

FIG. 25 shows another embodiment of a magnetic force system 78 that, in use, shortens an axis of a heart valve using one or more implanted magnets 80 and 82. In FIG. 25, the magnets 80 and 82 are not anchored on or above the annulus within the heart chamber occupied by the heart valve. Instead, the magnets 80 and 82 are placed outside the heart chamber to generate magnetic field forces that attract tissue regions of the annulus toward one another.

In the embodiment shown in FIG. 25, the heart valve comprises the mitral valve in the left atrium. A permanent magnet 80 is implanted either in the coronary sinus near the posterior annulus or on the septum in the right atrium close to the anterior annulus. In FIG. 25, the permanent magnet 80 is shown implanted in the coronary sinus. A second magnetic element 82 is implanted in the other location—here, on the septum in the right atrium close to the anterior annulus. The second magnetic element 82 can comprise a permanent magnet having a polarity opposite to the polarity of the first permanent magnet, or it can comprise a soft ferromagnetic material. The force of magnetic attraction between the permanent magnet 80 and the second magnetic element 82 draws the posterior annulus and the anterior annulus toward one another, shortening the minor axis.

Magnetic force systems 62 or 78 that shorten an axis of a heart valve can be deployed during an open surgical or thoracoscopic procedure. Alternatively, catheter-based approaches may also be used.

II. Implant Systems for Directly Lengthening the Major Annulus Axis While Directly Shortening the Minor Axis Any implant of the types just described can be used alone, to provide direct shortening along the minor axis of the annulus, which can also provide reactive lengthening of the annulus along its major axis.

Figure 26:
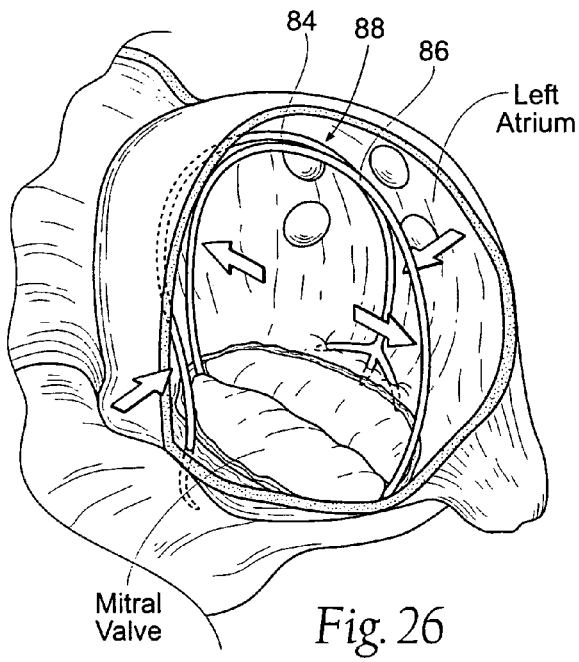
FIG. 26 is a lateral perspective view of the left atrium showing the implantation at or near a mitral valve of an implant along the major axis and an implant along the minor axis, forming a combined implant system that can concurrently lengthen the major axis and shorten the minor axis.
Figure 27:
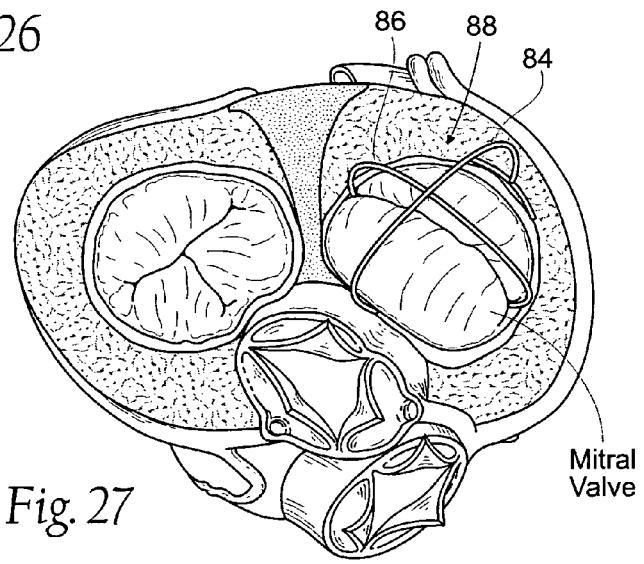
FIG. 27 is a superior view of the combined implant system and heart shown in FIG. 26.

As FIGS. 26 and 27 show, a given minor axis implant 84 may also be used in combination with a major axis implant 86, forming a combined implant system 88. In the system 88, the major axis implant 86 provides direct lengthening along the major axis of the annulus. In the system 88, the active lengthening of the major axis (by the major axis implant 86) is accompanied by the active shortening of the minor axis (by the minor axis implant 84). Use of the major axis implant 86 complements the minor axis implant 84, enhancing the reactive lengthening of the major axis occasioned by use of the minor axis implant 84.

Of course, the major axis implant 86 can be used alone. When used alone, the major axis implant 86 can reactively shorten in the minor axis, as well as correspondingly reshape other surrounding anatomic structures.

The major axis implant 86 can be sized and configured to achieve other objectives. The major axis implant 86 can, for example, be sized and configured to shorten the major axis. Alternatively, the major axis implant 86 can be sized and configured to merely stabilize tissue adjacent the heart valve annulus, without attendant lengthening or shortening of the major axis. As before stated, a major axis implant 86 of these alternative sizes and configurations can be used alone or in combination with a minor axis implant.

A. Elastic Implant Systems

1. Single Function Major Axis Implant Structures

In one representative embodiment (see FIGS. 26 and 27), e.g., for reshaping a mitral valve annulus, the major axis implant 86 is sized and configured as a single function component to rest along the major axis of the annulus above and/or along the valve annulus, alone or in combination with a single function minor axis implant 84. The major axis implant 86 can be of the type described in copending U.S. patent application Ser. No. 10/677,104, filed Oct. 1, 2003, and entitled "Devices, Systems, and Methods for Reshaping a Heart Valve Annulus," which is incorporated herein by reference.

Figure 28:
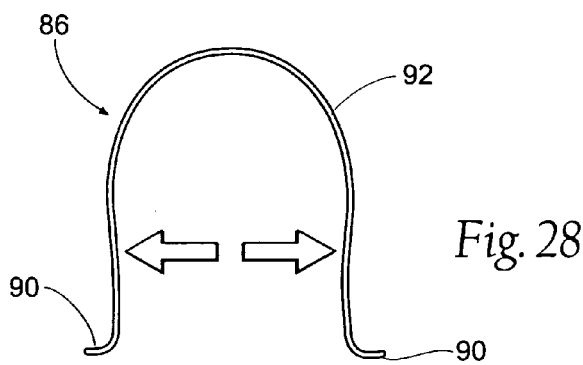
FIG. 28 is a side view of a representative embodiment of an implant that can be implanted along the major axis of a valve annulus in association with the system shown in FIGS. 26 and 27, the implant being sized to apply a direct mechanical force along the major axis of the annulus to lengthen the major axis.

As described in the above-identified application, the major axis implant 86 is desirably made—e.g., by bending, shaping, joining, machining, molding, or extrusion—from a biocompatible, super-elastic metallic material. As shown in FIG. 28, the major axis implant 86 includes a pair of struts 90 joined by an intermediate rail 92. As FIGS. 27 and 28 show, the struts 90 of the major axis implant 86 are sized and configured to rest in, at, or near the leaflet commissures. The superelastic material of the implant 86 is selected to possess a desired spring constant, which imparts to the rail 92 the ability to be elastically compressed into an elastically loaded condition resting in engagement with tissue in, at, or near the leaflet commissures. When in its elastically loaded, compressed condition, the rail 92 exerts opposing forces to the tissues in, at, or near the commissures through the struts 90, tending to outwardly displace tissue and stretch the annulus along its major axis.

Figure 29:
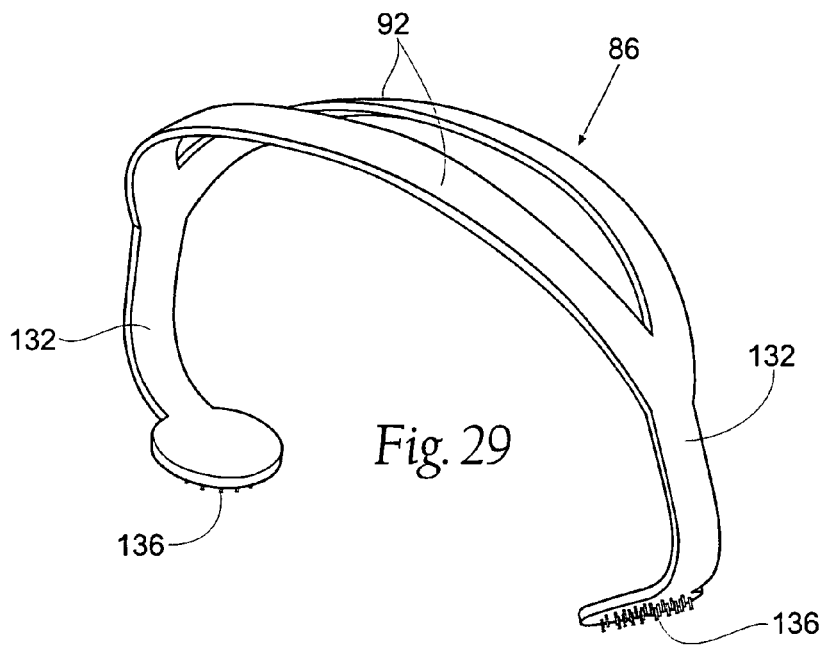
FIG. 29 is a side perspective view of an alternative embodiment of an implant that can be implanted along the major axis of a valve annulus in association with the system shown in FIGS. 26 and 27.
Figure 30:
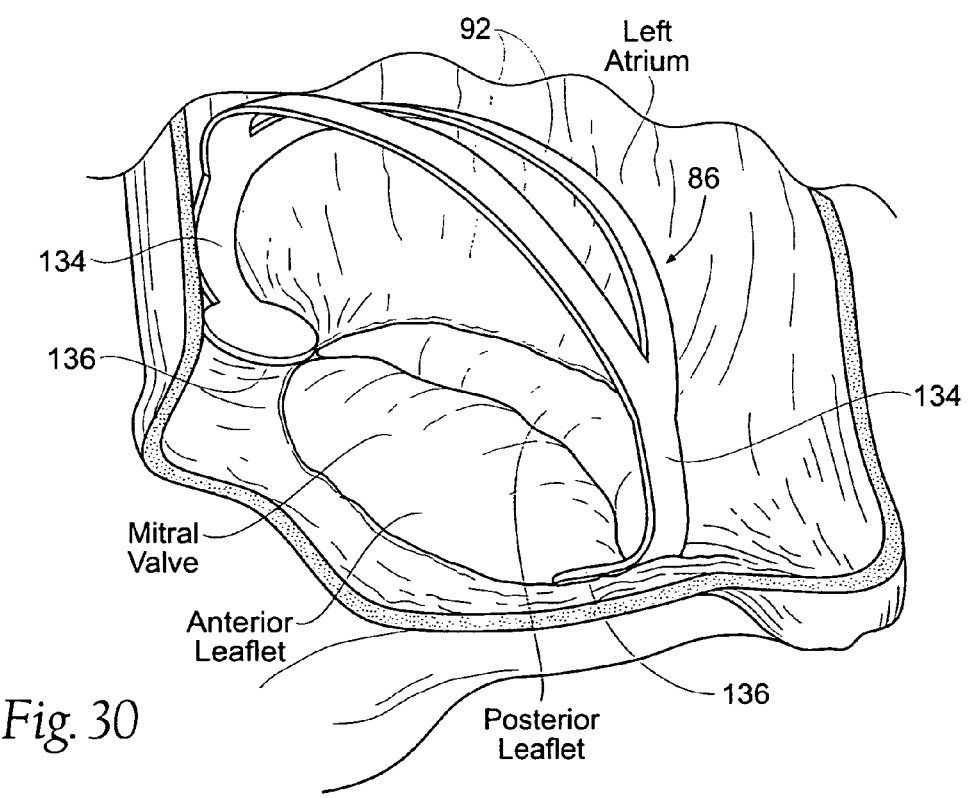
FIG. 30 is a lateral perspective view showing the implant shown in FIG. 29 implanted along the major axis of a mitral valve within the left atrium.

FIGS. 29 and 30 show another representative example of a single function major axis implant 86. The major axis implant 86 can be used alone (as FIGS. 29 and 30 show) or in association with a single function minor axis implant 84 to form a system 88 of the type shown in FIGS. 26 and 27. The implant 86 includes two rails 92 forming a closed rail structure. The rails 92 are supported by legs 134. The legs 134 are generally spaced 180° apart. In use (see FIG. 30), the implant 86 resides in the atrium above the mitral valve. The depending base of each leg 134 carries a fixation element 136. The fixation element 136 takes purchase in atrial tissue above and near to the commissures along the major axis of the annulus. The spring force of the legs 134 and rails 92 apply a spreading force that stretches tissue along the major axis. The high rails 92 protects against spreading of the leaflets.

In the illustrated embodiment, the fixation element 136 comprises a pad of barbs that penetrate atrial tissue above the annulus. However, other types of tissue engaging mechanisms can be used, e.g., roughened surfaces or tissue in-growth promoting materials. Placing numerous fixation elements 136 on legs 134 that engage tissue above the annulus makes it possible to reduce the force applied per unit of tissue area. Any fixation element 146 may, if desired, be combined with suture, an adhesive, or like material to further secure the implant.

Major axis implants 86 like that shown in FIGS. 29 and 30 can be located without the need to identify the exact position of the commissures. Adjustment of implant position after or during implantation is also facilitated, as there is no need to remove a strut from a commissure. Implants 86 like that shown in FIGS. 29 and 30 also present less chance of trauma or damage to tissue and anatomic structures beneath the annulus.

2. Mutiple Function Major and Minor Axis Implant Structures

Figure 31:
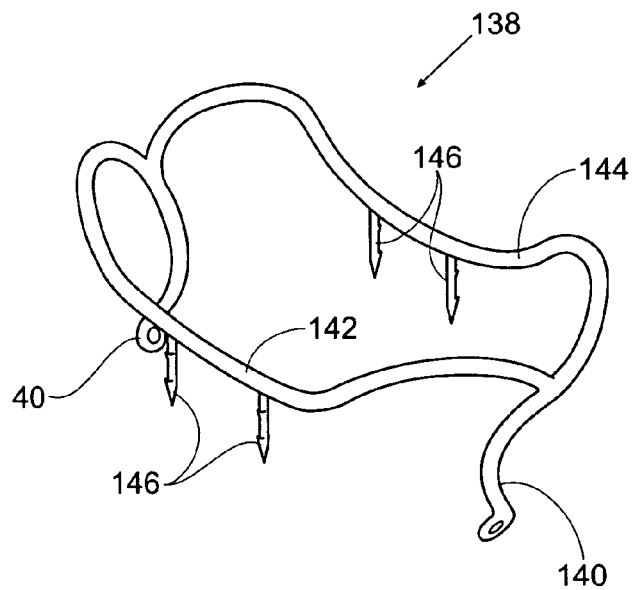
FIG. 31 is a side perspective view of a multiple function implant that is sized and configured to rest about a valve annulus to concurrently reshape the valve annulus along both major and minor axes, the implant in FIG. 31 having barbs that can be placed into contact with tissue at or near the annulus.
Figure 32:
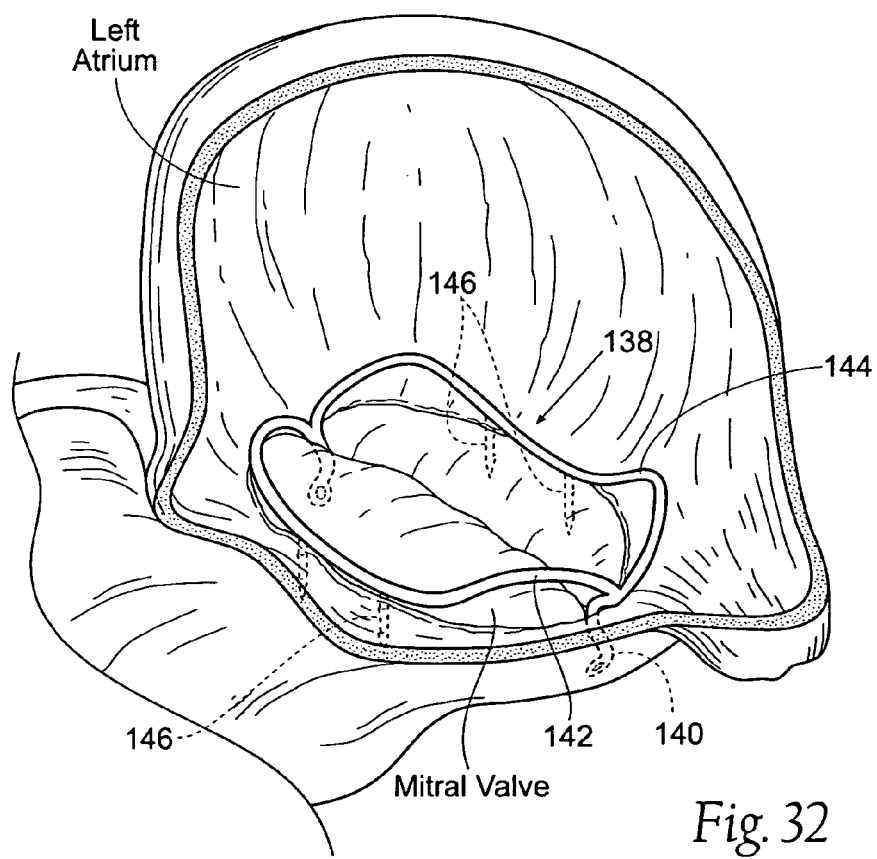
FIG. 32 is a lateral perspective view showing the implant shown in FIG. 31 implanted about a mitral valve within the left atrium.

In another representative embodiment (see FIG. 31), e.g., for reshaping a mitral valve annulus, a multi-function implant 138 can be sized and configured to rest about the annulus (as FIG. 32 shows) and function to reshape both major and minor axes.

The multi-function implant 138 is desirably made—e.g., by bending, shaping, joining, machining, molding, or extrusion—from a biocompatible, super-elastic metallic material. As shown in FIG. 31, the implant 138 includes a pair of struts 140 joined by a pair of oppositely spaced rails 142 and 144, forming a ring-like structure. The rails 142 and 144, of course, can take various shapes.

As FIG. 32 shows, the struts 140 of the implant 138 are sized and configured to rest in, at, or near the leaflet commissures. The superelastic material of the implant 138 is selected to possess a desired spring constant, which imparts to the rails 142 and 144 the ability to be elastically compressed into an elastically loaded condition resting in engagement with tissue in, at, or near the leaflet commissures. When in the elastically loaded, compressed condition, the rails 142 and 144 exert opposing forces to the tissues in, at, or near the commissures through the struts 140, tending to outwardly displace tissue and providing the function of stretching the annulus along its major axis. Alternatively, the struts 140 can comprise the legs and fixation elements shown in FIGS. 29 and 30, or other forms of tissue fixation mechanisms, to accommodate purchase in atrial tissue above the annulus, to perform the same function.

As FIG. 31 shows, the rails 142 and 144 include fixation elements 146, which, in the illustrated embodiment, take the form of tissue penetrating barbs. The fixation elements 146 on the rails 142 and 144 are sized and configured to take purchase in tissue in either annuluar, infra-annuluar or supra-annular tissue adjacent to, respectively, the anterior annulus and the posterior annulus (as FIG. 32 shows). The superelastic material of the implant 138 is selected to possess a desired spring constant, which imparts to the rails 142 and 144 the ability to be elastically stretched and placed into tension when resting in engagement with tissue adjacent the anterior annulus and posterior annulus. When in the elastically loaded, in-tension condition, the rails 142 and 144 exert opposing pulling forces on tissue at or near the annulus. This provides the function of shortening the annulus along its minor axis. The rails 142 and 144 can be expanded apart, e.g., by use of a balloon 148 placed between the rails 142 and 144 and inflated, placing the fixation elements 146 into contact with tissue. Collapsing the balloon allows the implant to assume its desired shape with the tissue attached.

Figure 33:
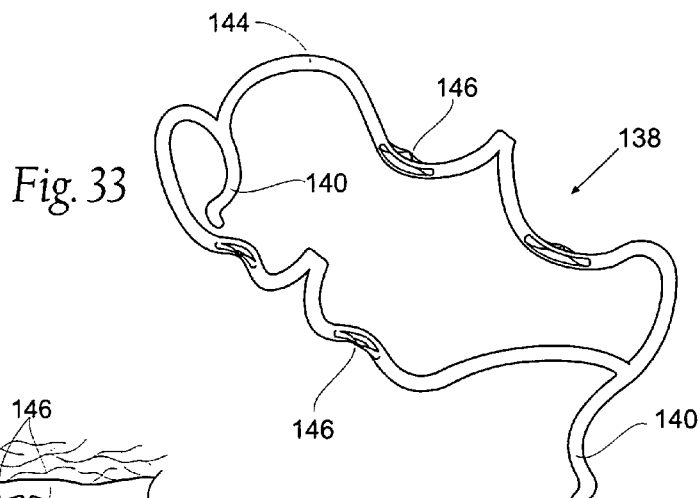
FIG. 33 is a side perspective view of an alternative embodiment of a multiple function implant that is sized and configured to rest about a valve annulus to concurrently reshape the valve annulus along both major and minor axes, the implant in FIG. 35 having inwardly folded barbs that can be outwardly folded by expansion of the implant into contact with tissue at or near the annulus.
Figure 34:
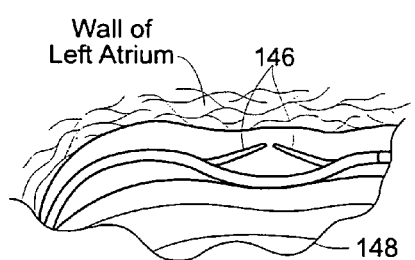
FIGS. 34, 35, and 36 are superior views of the outwardly folding of the barbs of the implant shown in FIG. 33 in response to the inflation of a balloon.
Figure 35:
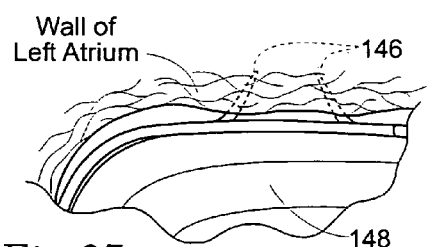
Figure 36:
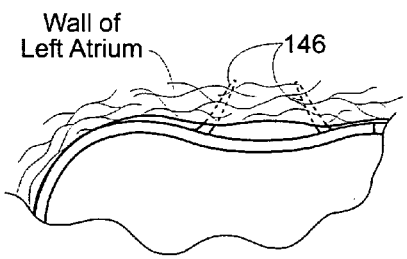
Figure 37:
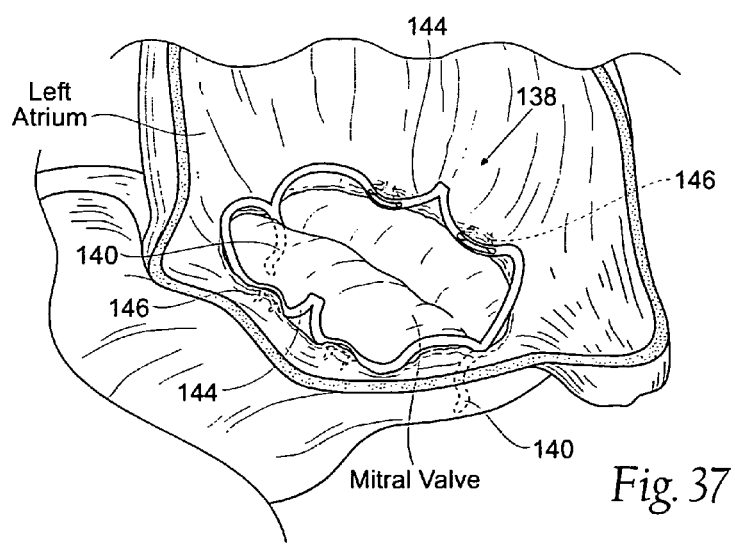
FIG. 37 is a lateral perspective view showing the implant shown in FIG. 33 implanted about a mitral valve within the left atrium.

Other types and forms of tissue fixation elements 146 can be used. For example, as shown in FIG. 33, the tissue fixation elements 146 can comprise barbs that are deployed in an inwardly folded condition. The barbs 146 can be outwardly folded when the rails 142 and 144 are expanded apart, e.g., by use of a balloon 148 placed between the rails 142 and 144 and inflated (see FIG. 34). Upon further inflation of the balloon 148 (see FIGS. 35 and 36), the barbs 146 are driven into in either infra-annuluar or supra-annular tissue adjacent to the anterior annulus and the posterior annulus (as FIG. 37 shows). The balloon 148 also places the rails 142 and 144 into tension, to perform their intended function of shortening the minor axis of the annulus.

In other embodiments, the tissue fixation elements 146 can take the form of pads with or without tissue penetrating members, and/or roughened surfaces and/or tissue in-growth promoting materials, such as polyester fabric. Any fixation element 146 may, if desired, be combined with suture, an adhesive, or like material to further secure the implant 138.

3. Implantation

Any of the single function implants 86 or multiple function implants 138 can be elastically straightened and/or folded to fit within a catheter or sheath for deployment, as generally shown in FIG. 10C. Alternatively, the single function implants 86 or multiple function implants 138 can be deployed during an open surgical or thoracoscopic procedure.

Figure 38A:
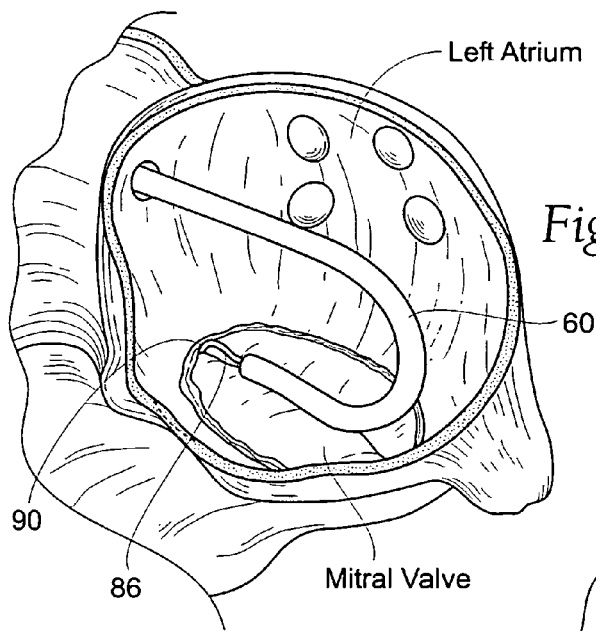
FIGS. 38A, 38B, and 38C are lateral perspective views of the sequential deployment of the implant shown in FIG. 28 from the catheter shown in FIGS. 10A, 10B, and 10C, the implant being deployed in compression across the major axis of the mitral valve in the left atrium.
Figure 38B:
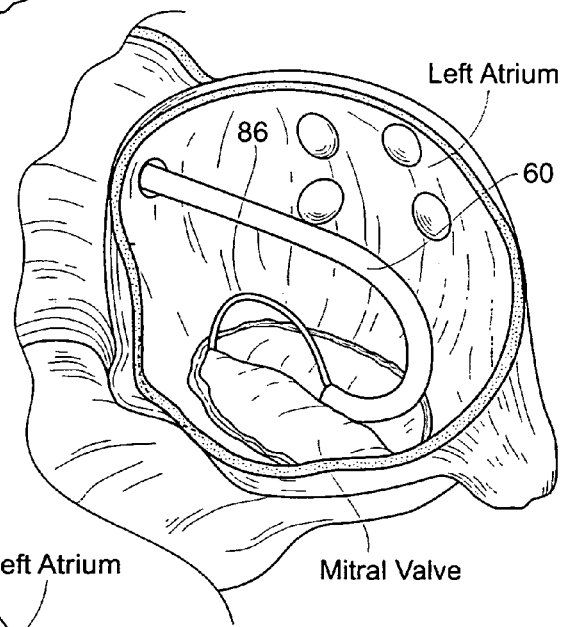
Figure 38C:
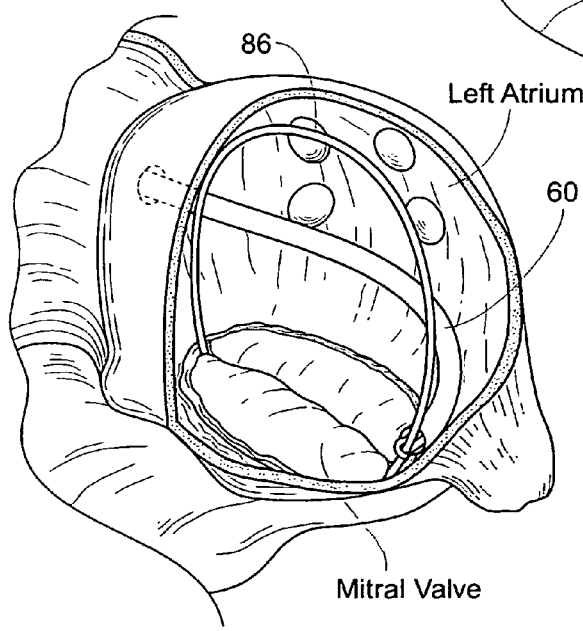

For example, with respect to the single function, major axis implant 86, access into the left atrium through the septum from the right atrium can be accomplished as shown in FIGS. 10A, 10B, and 10C. The implant delivery catheter 58 carries the major axis implant 86 in a sheath 60 at its distal end (see FIG. 38A), in a collapsed, straightened condition. As FIG. 38A shows, under image guidance, the strut 90 on the leading end of the major axis implant 86 is freed from the sheath 60 and seated retrograde in the medial commissure of the valve annulus. The sheath 60 is withdrawn in line with the coaptation line in a lateral direction along the coaptation line. Progressively freed from the sheath 60, the major axis implant 86 shapes and seats (as FIGS. 38B and 38C show), until the trailing strut 90 unfolds and seats within the lateral commissure. The implant 86 can also be positioned or repositioned under image guidance within the left atrium using a catheter-deployed grasping instrument.

Figure 39:
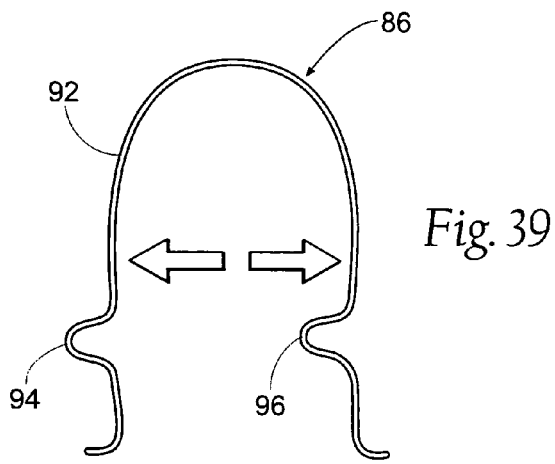
FIG. 39 is a side perspective view of an alternative embodiment of an implant that can be implanted along the major axis of a valve annulus in association with the system shown in FIGS. 26 and 27, the implant being sized and configured to rest at or near a heart valve annulus and apply a direct mechanical force along the major axis of the annulus to outwardly displace tissue away from the center of the annulus, the implant shown in FIG. 39 including bell-shaped protrusions that can be grasped to aid in the positioning and/or placement of the implant into compression.
Figure 40:
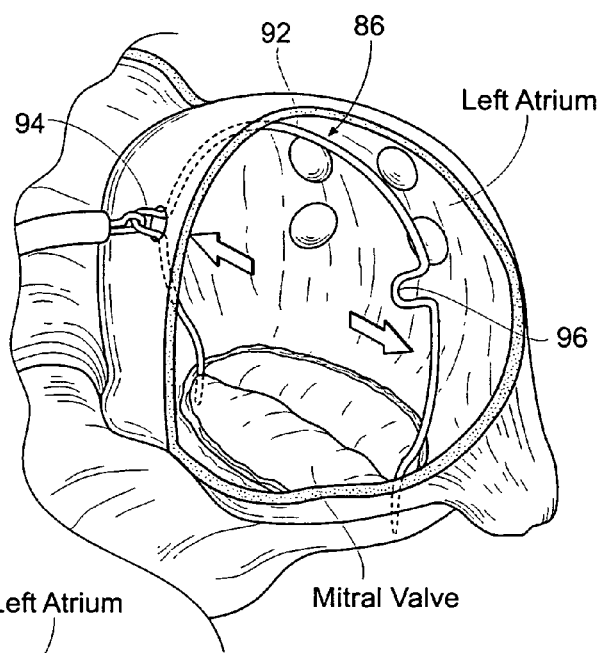
FIG. 40 is a lateral perspective view of the implant shown in FIG. 39 deployed at or near the mitral valve annulus in the left atrium, with one of the bell-shaped protrusions extending through and anchored to the septum in the right atrium.

In an alternative embodiment (see FIG. 39), the major axis implant 86 can include bell-shaped protrusions 94 and 96 formed along medial and lateral portions of the rail 92. As FIG. 40 shows, the medial protrusion 94 is sized and configured to extend through the septum and project into the right atrium. There, the medial protrusion 94 is exposed for engagement by a grasping instrument deployed in the right atrium. The grasping instrument in the right atrium can take hold of the protrusion 94 to facilitate placement of the rail 92 in compression within the left atrium. Barbed stays 98 can be crimped to the medial protrusion 94 to help maintaining compression on the rail 92. The medial grasping site, projecting into the right atrium, also facilitates repositioning and/or retrieval of the major axis implant 86. The lateral protrusion 96 can likewise be grasped by an instrument in the left atrium for placing the rail 92 in compression.

Figure 41:
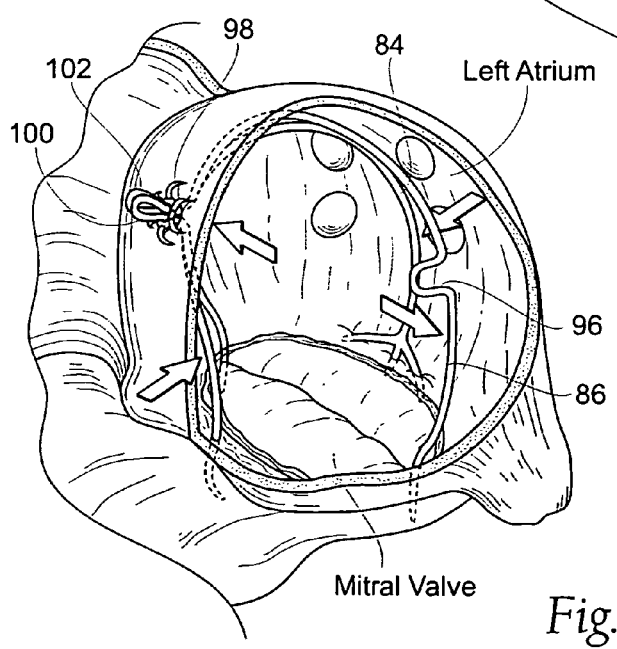
FIG. 41 is a lateral perspective view of a combined implant system of the type shown in FIG. 26 that can concurrently lengthen the major axis and shorten the minor axis, the system including a major axis implant and a minor axis implant both of which include a bell-shaped protrusion that extends through and is anchored to the septum in the right atrium.

As shown in FIG. 41, both the minor axis implant 84 and the major axis implant 86 can include grasping protrusions 100 and 102 that jointly project through the septum into the right atrium. Both protrusions 100 and 102 can be manipulated to place the minor axis implant 84 into tension and to place the major axis implant 86 into compression, as previously described, to achieve the desired reshaping of the annulus.

B. Elastic Implant-Magnetic Force Field Systems

Other types of systems that concurrently accomplish direct major and minor reshaping are possible. For example, FIG. 42 shows a representative embodiment of a system 104 that includes an elastic component 106, to provide direct reshaping along one axis of a valve annulus, and a magnetic force field component 108, to provide direct reshaping along another axis of the valve annulus.

In the embodiment shown in FIG. 42, the valve to be reshaped is the mitral valve in the left atrium. In this arrangement, the elastic component 106 comprises an elastic major axis implant of the type already described (e.g., as shown in FIG. 30 or 39), which is sized and configured to rest along the major axis of the annulus above and/or along the valve annulus. As previously described, the elastic major axis implant 106 stretches the annulus along the major axis.

In this arrangement, the magnetic force field component 108 comprises magnetic elements 132 of the type previously described (e.g., as shown in FIGS. 21A to 21E). The magnetic elements 132 are located in a spaced-apart relationship across the minor axis on or above the anterior annulus and the posterior annulus. The magnetic elements 132 can comprise two permanent magnets of opposite polarity, or one permanent magnet and one soft ferromagnetic material. In the illustrated embodiment, the magnetic elements 132 are stabilized at opposite ends of a yoke 110 coupled to the elastic major axis implant 106 near one of its struts. The magnetic elements 132 are implanted in tissue on or above the annulus. The force of magnetic attraction between the magnet components 132 draws the posterior annulus and the anterior annulus toward one another, shortening the minor axis.

The yoke 110 supporting the magnetic elements 132 may possess a spring constant. Placing the yoke 110 into tension at the time the magnetic elements 132 are implanted on or above the annulus provides an auxiliary mechanical force, to augment the magnetic force serving to shorten the minor axis.

III. Annuloplasty Systems

A. Point Loading

FIG. 43 shows a point loaded annuloplasty system 112 for reshaping a heart valve annulus. The system 112 applies a mechanical force about the perimeter of the heart valve annulus. The mechanical force pulls on the annulus to restore a generally oval shape conducive to leaflet coaptation. For purpose of illustration, FIG. 43 shows the heart valve annulus as comprising the mitral valve in the left atrium.

In FIG. 43, the system 112 creates the mechanical force by circumferentially linking adjacent sites on or above the annulus with a biocompatible elastic frame 114. In the illustrated embodiment, the frame 114 comprises an elastic material, such as Selastic material. The frame 114 links the sites by threading through a network of fasteners 116 that are inserted into tissue on or above the annulus. FIGS. 44A to 44C show representative embodiments of the fasteners 116, which include clip components 118 to accommodate passage of the frame 114 and barbs 120 that secure the clip components 118 to tissue. The elastic frame 114 is in tension within the network of fasteners 116. The tension applied by the frame 114 pulls tissue in or along the annulus together, thereby tightening the annulus to restore a non-dilated shape.

Figure 45:
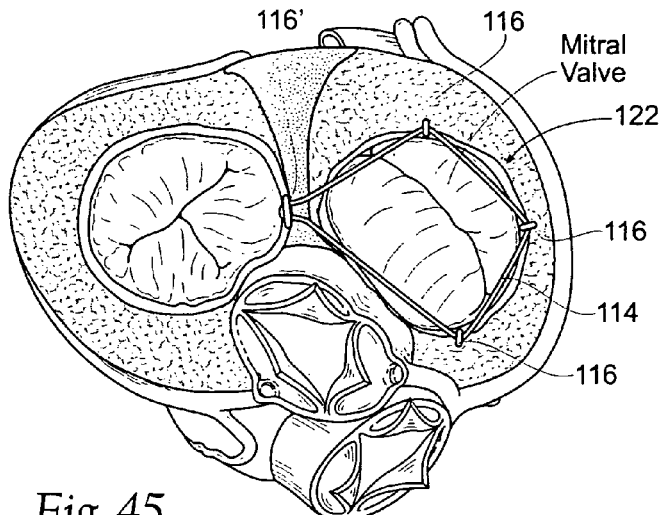
FIG. 45 is a superior section view of a heart showing the installation of an alternative embodiment of a point loaded annuloplasty system about the mitral valve annulus, the system shown in FIG. 45 having a point attachment in the right atrium across the septum.

An alternative embodiment of a point loading annuloplasty system 122 is shown in FIG. 45. In FIG. 45, as in FIG. 43, an elastic frame 114 is placed into tension through a network of fasteners 116 that are inserted into tissue on or above the annulus. In FIG. 43, all of the fasteners 116 were located in or along the annulus. In FIG. 45, one fastener 116' is located in the right atrium outside the left atrium. The fastener 116' engages the septum. In this arrangement, the frame 114 passes through the septum, pulling laterally on the septum toward the left atrium to reshape tissue along the anterior annulus.

B. Commissural Annuloplasty

Figure 46:
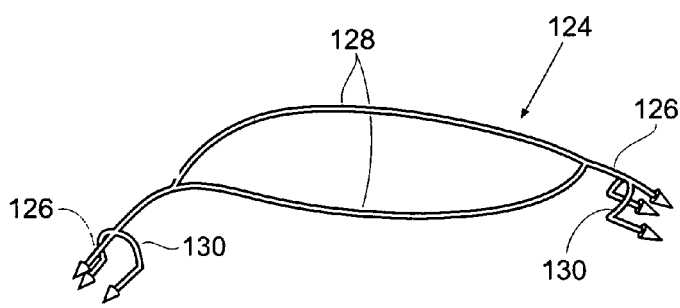
FIG. 46 is a perspective view of an implant sized and configured to perform commissural annuloplasty at or near the mitral valve in the left atrium, the implant having elastic jaws that squeeze the annulus together at the commissures to promote leaflet coaptation.
Figure 47:
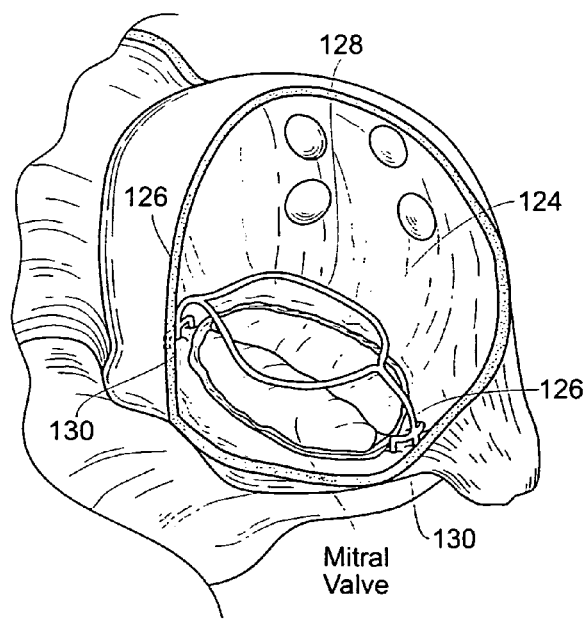
FIG. 47 is a lateral perspective view of the left atrium, showing the placement of the implant shown in FIG. 46 in the mitral valve to perform commissural annuloplasty.

FIG. 46 shows an implant 124 for performing commissural annuloplasty. As FIG. 47 shows, the implant 124 is sized and configured, in use, to rest along the major axis of a heart valve annulus above and/or below the valve annulus. In the illustrated embodiment (see FIG. 47), the implant 124 rests along the major axis of a mitral valve annulus in the left atrium.

The implant 124 is desirably made—e.g., by bending, shaping, joining, machining, molding, or extrusion—from a biocompatible metallic or plastic material. As shown in FIG. 39, the implant 124 includes a pair of struts 126 joined by an intermediate rail 128.

As FIG. 47 shows, the struts 126 are sized and configured to rest in either an infra-annular or a supra-annular position at or near the annulus adjacent the medial and lateral leaflet commissures.

Figure 48A:
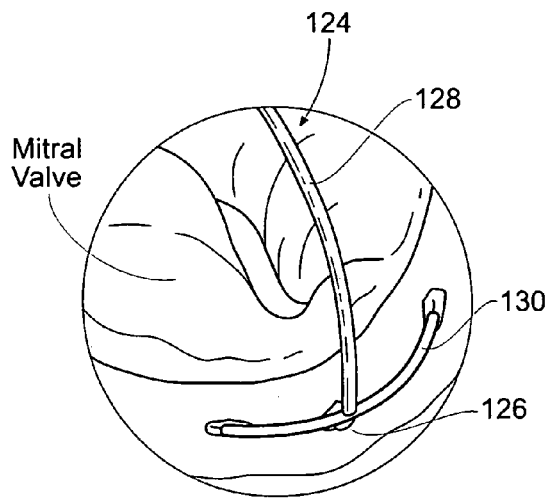
FIGS. 48A and 48B are enlarged superior views of the elastic jaws that the implant shown in FIG. 46 includes to create pulling forces at a commissure, FIG. 48A showing the jaws spread apart to engage tissue at or near a commissure, and FIG. 48B showing the jaw in an in-tension condition to squeeze the annulus together at the commissure to promote leaflet coaptation.

The implant 124 includes a jaw 130 that is appended to each strut 126. The jaws 130 are made from an elastic material. Each jaw 130 is sized and configured to possess a normal, unloaded, shape or condition (shown in FIG. 46). In this condition, the jaw 130 is not in compression or tension. The material of each jaw 130 is selected to possess a desired spring constant. The spring constant imparts to each jaw 130 the ability to be elastically spread apart (see FIG. 48A) and placed in tension out of its normal, unloaded, condition, in response to external stretching forces applied to the jaws 130.

Figure 48B:
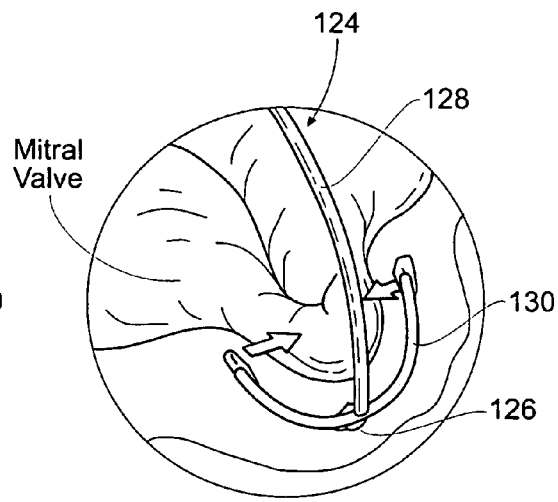

When the jaws 130 are anchored in tissue in a stretched apart condition at or near the commissures (see FIGS. 48A and 48B), the jaws 130 assumes an elastically loaded, in-tension condition. When in this elastically loaded, in-tension condition, the jaws 130 exert opposing pulling forces on tissues at or near the commissures. These forces are shown by arrows in FIG. 48B. The pulling forces inwardly displace tissue at the commissures, squeezing the annulus together at the commissures to promote leaflet coaptation.

The implant 124 can rest as shown in FIG. 47 without being in compression and/or tension, thereby itself applying no pushing or pulling force upon tissue along either the major or minor axes of the annulus. Alternatively, the implant 124 can be made of an elastic material. This imparts to the rail 128 the ability to be compressed into an elastically loaded condition resting in engagement with tissue in, at, or near the leaflet commissures. When in this condition, the rail 124 can exert opposing forces to the tissues in, at, or near the commissures through the struts 126, tending to outwardly displace tissue and stretch the annulus along its major axis.

Figure 49:
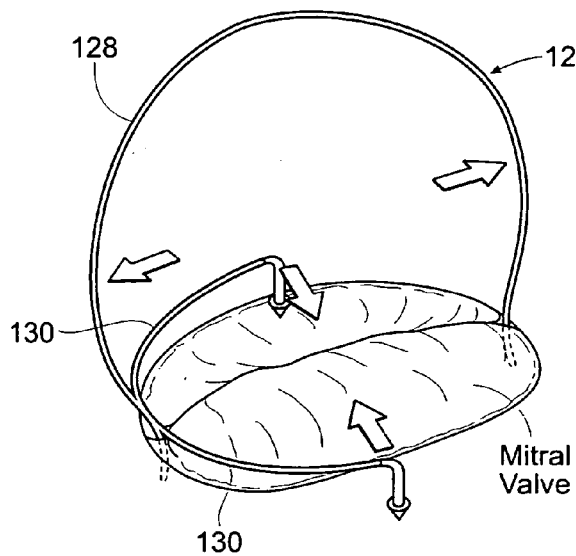
FIG. 49 shows an anterior perspective view of a mitral valve in which a structural variation of the implant shown in FIG. 46 has been implanted, the structural variation having elastic jaws that have been lengthened and shaped to follow the medial and lateral contours of the annulus to be placed into tension across the minor axis of the annulus to provide a mechanical force that shortens the minor axis in the manner shown in FIG. 9.

Furthermore, as shown in FIG. 49, one or both of the jaws 130 of the implant 124 can be lengthened and shaped to follow the medial and lateral contours of the annulus, terminating in an oppositely facing relationship on the anterior annulus and posterior annulus, similar to the yoke 110 shown in FIG. 42. In this arrangement, the jaws 130 possess a spring constant. Placing the jaws 130 in tension across the minor axis of the annulus (as FIG. 49 shows) at the time of implantation provides a mechanical force that shortens the minor axis, in the manner previously described. The jaws 130 can be further lengthened and shaped to form a full ring-like structure.

Figure 50:
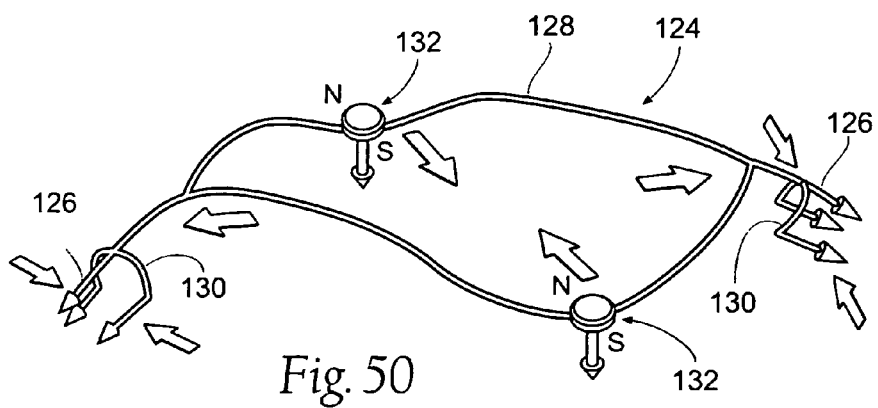
FIG. 50 shows a perspective view of a variation of the implant shown in FIG. 46, which includes a ring-like structure that carries magnetic elements, to provide a magnetic force that shortens the minor axis in the manner shown in FIG. 18A.

As shown in FIG. 50, the implant 124 can be used in association with a magnetic force field component 132 of the type previously described (e.g., as shown in FIGS. 21A to 21E). The magnetic components 132 are located in a spaced-apart relationship across the minor axis on or above the anterior annulus and the posterior annulus. The magnetic components 132 can comprise two permanent magnets of opposite polarity, or one permanent magnet and one soft ferromagnetic material. In the illustrated embodiment, The magnetic components 132 are implanted in tissue on or above the annulus. The force of magnetic attraction between the magnet components 132 draws the posterior annulus and the anterior annulus toward one another, shortening the minor axis.

Based upon the foregoing, it is apparent that implant systems can be provided that affect direct shortening of the minor axis, and/or direct lengthening of the major axis, alone or in combination using various mechanical and/or magnetic means. It is also apparent that shaping of a heart valve annulus can be accomplished by mechanical and/or magnetic force applied circumferentially about the annulus, and/or by reshaping tissue at the commissures, alone or in combination with mechanical and/or magnetic forces that reshape the annulus along its major axis and/or minor axis.

While the new devices and methods have been more specifically described in the context of the treatment of a mitral heart valve, it should be understood that other heart valve types can be treated in the same or equivalent fashion. By way of example, and not by limitation, the present systems and methods could be used to prevent or reduce retrograde flow in any heart valve annulus, including the tricuspid valve, the pulmonary valve, or the aortic valve. In addition, other embodiments and uses of the invention will be apparent to those skilled in the art from consideration of the specification and practice of the invention disclosed herein. The specification and examples should be considered exemplary and merely descriptive of key technical; features and principles, and are not meant to be limiting. The true scope and spirit of the invention are defined by the following claims. As will be easily understood by those of ordinary skill in the art, variations and modifications of each of the disclosed embodiments can be easily made within the scope of this invention as defined by the following claims.

What is claimed is:

1. A method comprising
identifying for treatment a heart having a right atrium and a left atrium separated by an interatrial septum, the left atrium including a mitral valve having an annulus with a minor axis with a native length extending along an annular plane in a posterior-to-anterior direction within the left atrium,
providing an implant comprising a rail portion, a posterior portion joined to the rail portion, and an anterior portion joined to the rail portion,
deploying the implant through an intravascular path from the right atrium through the interatrial septum into the left atrium including
positioning the anterior portion of the implant entirely inside the heart and solely within the right atrium in contact solely with the interarterial septum above an anterior region of the annulus,
positioning the posterior portion of the implant entirely inside the heart and solely within the left atrium in contact solely with tissue above a posterior region of the annulus, and
positioning the rail portion of the implant entirely inside the heart and solely within the left atrium in a path that spans across the minor axis of the annulus between the posterior region above the annulus and the interarterial septum above the anterior region of the annulus, and
shortening the native length of the minor axis of the annulus including
anchoring the posterior portion of the implant solely to tissue inside the heart in a wall of the left atrium above the posterior region of the annulus, and
pulling on the anterior portion of the implant from within the right atrium to place the rail portion in tension within the left atrium, whereby the pulling exerts a pulling force on tissue within the left atrium at or near the posterior region of the annulus to draw the posterior region of the annulus inwardly toward the anterior region of the annulus without exerting a pulling force on the anterior region of the annulus, to thereby shorten the annulus along the minor axis, and
anchoring the anterior portion of the implant solely to tissue in the interatrial septum solely within the right atrium above the anterior region of the annulus to hold the tension on the rail portion.

2. A method according to claim 1, wherein the rail portion comprises a wire-form structure.

3. A method according to claim 1, wherein the rail portion comprises an elastic material.

4. A method according to claim 1, wherein the deploying the implant includes collapsing the implant for placement within a catheter.

5. A method according to claim 1, wherein anchoring the anterior portion includes coupling a tissue-engaging fixation element on the anterior portion solely within the right atrium above the anterior region of the annulus.